United States Patent
Kumar et al.

(10) Patent No.: US 8,536,337 B2
(45) Date of Patent: *Sep. 17, 2013

(54) SOLID FORMS OF METHYL (7AS,2'S)-2-(2-CHLOROPHENYL)-2-(2,4,5,6,7,7A-HEXAHYDROTHIENO[3,2-C]-5-PYRIDIN-2-ONE)ACETATE

(75) Inventors: Ashok Kumar, Mumbai (IN); Satish Rajanikant Soudagar, Mumbai (IN); Nellithanath Thankachen Byju, Mumbai (IN); Gaurav Sahal, Mumbai (IN); Arpana Prashant Mathur, Mumbai (IN); Sanjay Pandurang Gawade, Mumbai (IN); Dinesh Kanji Bhadra, Mumbai (IN); Devki Moje, Mumbai (IN)

(73) Assignee: IPCA Laboratories Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/428,657

(22) Filed: Mar. 23, 2012

(65) Prior Publication Data

US 2012/0329763 A1    Dec. 27, 2012

Related U.S. Application Data

(63) Continuation of application No. 13/345,360, filed on Jan. 6, 2012.

(51) Int. Cl.
*C07D 513/04* (2006.01)
*A61K 31/4436* (2006.01)

(52) U.S. Cl.
USPC .......................................... 546/114; 514/301

(58) Field of Classification Search
USPC .......................................... 546/114; 514/301
See application file for complete search history.

(56) References Cited

PUBLICATIONS

Savi "Identification and Biological Activity of the Active Metabolite of Clopidogrel." Thromb Haemost 2000; 84: 891-6 AND.*
Testa "The Biochemistry of Drug Metabolism—An Introduction Part 5. Metabolism and Bioactivity." Chemistry & Biodiversity—vol. 6 (2009) 591-683.*
West, Anthony R., Solid State Chemistry and its Applications, Wiley, New York, 1988, pp. 358 & 365.*
Hornfeldt, Anna B. "Tautomeric properties and some reactions of the 2-hydroxythiophene and the 2-hydroxyfuran systems." 1968 Svensk Kemisk Tidskrift 80(10) 343-56.*
Hagihara, et al., "Comparison of Human Cytochrome P450 Inhibition by the Thienopyridines Prasugrel, Clopidogrel, and Ticlopidine," Drug Metabolism and Pharmacokinetics, 2008, pp. 412-420, vol. 23, No. 6, Japanese Society for the Study of Xenobiotics, Tokyo, Japan.
Tuffal, et al., "An Improved Method for Specific and Quantitative Determination of the Clopidogrel Active Metabolite Isomers in Human Plasma," Thrombosis and Haemostasis, 2011, pp. 696-705, vol. 105, No. 4, Schattauer Publishers, Stuttgart, Germany.
Farid, et al., "The Disposition of Prasugrel, a Novel Thienopyridine, in Humans," Drug Metabolism & Disposition, 2007, pp. 1096-1104, vol. 35, No. 7, The American Society for Pharmacology and Experimental Therapeutics, Bethesda, Maryland, USA.
Periello, et al., "Structure and Stereochemistry of the Active Metabolite of Clopidogrel," Drug Metabolism & Disposition, 2002, pp. 1288-1295, vol. 30, No. 11, The American Society for Pharmacology and Experimental Therapeutics, Bethesda, Maryland, USA.
Cardinal, et al., "The Electronic Aggregometer: A Novel Device for Assessing Platelet Behavior in Blood," Journal of Pharmacological Methods, 1980, pp. 135-158, vol. 3, Elsevier, Maryland Heights, MO, USA.
Schumacher, et al., "Biomarker Optimization to Track the Antithrombotic and Hemostatic Effects of Clopidogrel in Rats," Journal of Pharmacology and Experimental Therapeutics, 2007, pp. 369-377, vol. 322, No. 1, The American Society for Pharmacology and Experimental Therapeutics, Bethesda, Maryland, USA.
Tanaka, et al., "Z-335, a New Thromboxane A2 Receptor Antagonist, Prevents Arterial Thrombosis Induced by Ferric Chloride in Rats," European Journal of Pharmacology, 2000, pp. 413-418, vol. 401, Elsevier, Maryland Heights, MO, USA.
Nishiya, et al., "Mechanism-Based Inhibition of Human Cytochrome P450 2B6 by Ticlopidine, Clopidogrel, and the Thiolactone Metabolite of Prasugrel," Drug Metabolism and Disposition, 2009, pp. 589-593, vol. 37, No. 3.
Hagihara, et al., "A Possible Mechanism for the Differences in Efficiency and Variability of Active Metabolite Formation from Thienopyridine Antiplatelet Agents, Prasugrel and Clopidogrel," Drug Metabolism and Disposition, 2009, pp. 2145-2152, vol. 37, No. 11.
Farid, et al., "Metabolism and Disposition of the Thienopyridine Antiplatelet Drugs Ticlopidine, Clopidogrel, and Prasugrel in Humans," The Journal of Clinical Pharmacology, 2010, pp. 126-142, vol. 50.
Kazui, et al., "Identification of the Human Cytochrome P450 Enzymes Involved in the Two Oxidative Steps in the Bioactivation of Clopidogrel to Its Pharmacologically Active Metabolite," Drug Metabolism and Disposition, 2010, pp. 92-99, vol. 38, No. 1.
Velder, et al., "A Scalable Synthesis of (±)-2-Oxoclopidogrel," Synlett, 2010, pp. 467-469, No. 3.

* cited by examiner

*Primary Examiner* — David K O Dell
(74) *Attorney, Agent, or Firm* — Baker & Hostetler LLP

(57) ABSTRACT

New compounds, namely, (7aS,2'S)-2-oxoclopidogrel and its pharmaceutically acceptable salts thereof are disclosed for treatment or prophylaxis of thrombo-embolism and/or cardiovascular diseases.

16 Claims, 11 Drawing Sheets

SOLID FORMS OF METHYL (7AS,2'S)-2-(2-CHLOROPHENYL)-2-(2,4,5,6,7,7A-HEXAHYDROTHIENO[3,2-C]-5-PYRIDIN-2-ONE)ACETATE

CROSS-REFERENCE TO RELATED APPLICATIONS

The present application is a continuation of U.S. patent application Ser. No. 13/345,360, filed Jan. 6, 2012, which claims priority to Indian Patent Application No. 1848/MUM/2011, filed Jun. 27, 2011, the entire disclosure of which is incorporated by reference herein.

TECHNICAL FIELD OF INVENTION

The present invention relates to anti-thrombotic compounds, specifically substantially pure isomer of an intermediate metabolite of clopidogrel, namely, (7aS,2'S)-2-oxoclopidogrel and its pharmaceutically acceptable salts thereof. The present invention also relates to a method of ameliorating the drawbacks of the anti-platelet drug, clopidogrel, said method comprises administration of isolated substantially pure isomer of (7aS,2'S)-2-oxoclopidogrel in its free or pharmaceutically acceptable salt form for alleviating the symptoms of thrombosis and/or embolism by inhibiting blood platelet aggregation.

BACKGROUND OF THE INVENTION

Conditions resulting from thrombotic or thromboembolic events are the leading causes of illness and death in adults in western civilization. Intravascular thrombosis and embolism are common clinical manifestations of many diseases. Unregulated activation of the hemostatic system has the potential to cause thrombosis and embolism, which can reduce blood flow to critical organs like the brain and myocardium. Certain patient groups have been identified that are particularly prone to thrombosis and embolism. These include patients (1) immobilized after surgery, (2) with chronic congestive heart failure, (3) with atherosclerotic vascular disease; (4) with malignancy, or (5) who are pregnant. The majority of "thrombosis prone" individuals have no identifiable hemostatic disorder, although there are certain groups of individuals having inherited or acquired "hypercoagulable" or "prethrombotic" conditions predisposing them to recurrent thrombosis (Harrison's Principles of Internal Medicine, 12th ed. McGraw Hill).

Effective primary hemostasis requires three critical events: platelet adhesion, granule release, and platelet aggregation. Within a few seconds of injury, platelets adhere to collagen fibrils in vascular sub endothelium. This interaction is facilitated by von Willebrands factor, an adhesive glycoprotein which allows platelets to remain attached to the vessel wall despite the high shear forces generated within the vascular lumen. Von Willebrand's factor accomplishes this task by forming a link between platelet receptor sites and subendothelial collagen fibrils.

As the primary hemostatic plug is, being formed, plasma coagulation proteins are activated to initiate secondary hemostasis. There is little difference between hemostatic plugs, which are a physiological response to injury, and pathologic thrombi. Thrombosis is often described as coagulation which has occurred in the wrong place or at the wrong time. Hemostatic plugs or thrombi that form in veins where blood flow is slow are richly endowed with fibrin and trapped red blood cells and contain relatively few platelets. These thrombi often form in leg veins and can break off and embolize to the pulmonary circulation. Conversely, clots that form in arteries under conditions of high flow are predominantly composed of platelets and have little fibrin. These arterial thrombi may readily dislodge from the arterial wall and embolize to distant sites to cause temporary or permanent ischemia. This is particularly common in the cerebral and retinal circulation and may lead to transient neurologic dysfunction (transient ischemic attacks) including temporary monocular blindness (amaurosis fugax) or strokes. In addition, there is increasing evidence that most myocardial infarctions are due to thrombi which form within atherosclerotic coronary arteries. (The preceding discussion is taken primarily from Harrison's Principles of Internal Medicine, 12th ed., McGraw Hill.

Extracellular nucleotides and their receptors of platelets are important components of the cardiovascular system and are involved in functions like platelet activation and the control of vascular tone. Adenosine diphosphate (ADP) and Adenosine Triphosphate (ATP), are playing crucial roles in the physiological process of haemostasis and in the development and extension of arterial thrombosis (2). By itself ADP is a weak agonist of platelet aggregation inducing only reversible responses as compared to strong agonists such as thrombin or collagen. However, due to its presence in large amounts in the platelet dense granules and its release upon activation at sites of vascular injury, ADP is an important so-called secondary agonist which amplifies most of the platelet responses and contributes to the stabilization of the thrombus. The receptors for extracellular nucleotides belong to the P2 family which consists of two classes of membrane receptors: P2X ligand-gated cation channels (P2X1-7) and Glycoprotein-coupled P2Y receptors (P2Y1,2,4,6,11,12,13,114). Each of these receptors has a specific function during platelet activation and aggregation, which naturally has implications for their involvement in thrombosis.

Since ADP and ATP play a crucial role in platelet activation, their receptors are potential targets for antithrombotic drugs. The ATP-gated cation channel P2X1 and the two G protein-coupled ADP receptors, P2Y1 and P2Y12, selectively contribute to platelet aggregation and formation of a thrombus. Owing to its central role in the growth and stabilization of a thrombus, the P2Y12 receptor is an established target of antithrombotic drugs mainly the thienopyridine class of compounds like ticlopidine, Clopidogrel, prasugrel etc. . . . .

The mainstay of antiplatelet therapy for patients with acute coronary syndromes (ACS), including those undergoing early percutaneous coronary intervention (PCI) and stents implantation is administration of a combination of Aspirin and clopidogrel. Aspirin inhibits platelet thomboxane A2 production and platelet activation, and reduces the risk of recurrent ischemic events in patients at high risk of vascular events by 22% (absolute risk reduction (ARR) about 2%) at the expense of an increase in the odds of major bleeding events by about 60% (Absolute risk increase (ARI) about 0.5%. Clopidogrel inhibits ADP induced platelet activation by blocking the platelet receptor P2Y12, which when combined with Aspirin therapy in patients with ACS, reduces the risk of recurrent ischemic events by a further 20% (ARR about 2.1%), in which the major bleeding events are not increased statistically from aspirin monotherapy.

Clopidogrel (Formula I), chemically named as "'(+)-(S)-methyl2-(2-chlorophenyl)-2-(6,7-dihydrothieno[3,2-c]pyridin-5(4H)-yl)acetate", is currently considered to be the gold standard in the inhibition of blood platelet aggregation. Clopidogrel is marketed as its hydrogen sulphate, hydrochloride, and benzene sulphonate salts. It is widely used for controlling the ischemic events and other cardiovascular disorders efficiently for last 12 years or more.

Formula 1:

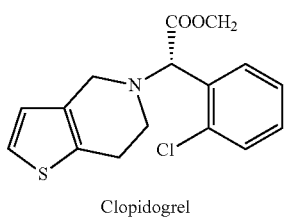

Clopidogrel

However, clopidogrel has several potential limitations. First, the onset of action is delayed and a time lag between administration and therapeutic activity is observed. A therapeutically significant level of 50% inhibition of ADP induced platelet aggregation, as measured by light transmission aggregometry (LTA) (5 μM ADP ex-vivo) is not reached until 4-6 hours after administration of a loading dose of 300 mg clopidogrel or until 2 hours by doubling the dose to 600 mg. Secondly, there is a dose ceiling effect, as tripling the dosing from regular dose of 300 mg to 900 mg produces only 60% inhibition of ADP induced platelet aggregation (at 5 μM ADP), and less than 50% inhibition of platelet aggregation (induced by 20 μM of ADP (ex vivo)). Third, almost all clinical trials involving clopidogrel reveal that therapeutic levels of platelet inhibition are not achieved in a majority of patients because of large inter-individual variability in response to clopidogrel treatment. This patient population is referred as 'non-responders' or 'poor responders' to clopidogrel. Non-responders make up about 14% of the ethnic Chinese population and 3-4% among Caucasians. Overall, poor responders are close to 23% or the total patient population, and variation of inhibitory activity is reported in about 45% of the total patient population. The ultra rapid metabolism of clopidogrel has been reported in patients having a specific phenotype of CYP isoform (about 4%-18% patients) which leads to more severe bleeding episodes, with higher platelet aggregation. Considering these wide variability and data from clinical trials, the FDA requires that a boxed warning be included in the label of clopidogrel highlighting the ineffectiveness of clopidogrel in certain classes of patients and suggesting screening of patients for genotyping to identify poor responders to clopidogrel before treatment.

It has been found that the variations in the inhibitory activity of clopidogrel originates from the difference in the activity of liver enzymes that metabolize clopidogrel and also due to the limited intestinal absorption of clopidogrel, being a P-glycoprotein substrate. Upon ingestion of clopidogrel, it undergoes a series of metabolic reactions to produce metabolites. These reactions are mediated by CYP 450 as well as by action of hepatic human carboxyl esterase (hCE). The metabolic pathway of clopidogrel is set out below (Schemer). The use oldie specific metabolites as therapeutic agents for administration to patients in place of clopidogrel has not been suggested previously.

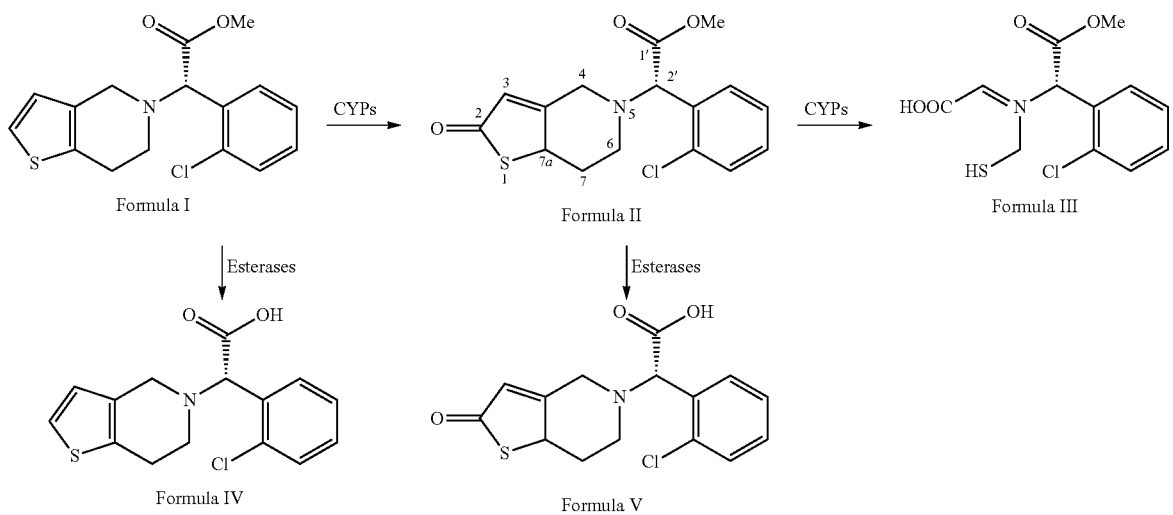

Scheme 1: Metabolic path of clopidogrel

Treatment of patients with a recently approved drug, namely, prasugrel rendered them susceptible to bleeding episodes, which may be life threatening, restricting its application in patients having a body weight of less than 60 kg and age of more than 75 years. Prasugrel has also been found to increase liver disease/toxicity in patients who are at risk of cirrhosis and thus, pharmacovigilance is suggested by FDA and is also a suspected carcinogen. As far as these severe side effects are concerned, clopidogrel is comparatively safer, resulting generally in lesser bleeding and liver toxicity. Further, the incidence of cardiovascular deaths is greatly reduced following treatment with clopidogrel in comparison to prasugrel and thus improvements in the efficacy of clopidogrel are likely to reduce the risk of thrombosis and/or embolism in patient groups much better than other structurally modified drugs.

(2'S)-2-oxo-clopidogrel is an intermediate metabolite formed during the oxidative metabolic step, as shown in above scheme. The active metabolite of clopidogrel has the structure given in formula III, and it has been documented that only one of the isomer is found to inhibit platelet, however, its absolute configuration is not yet determined. Active metabolite of 4R,1'S-isomer is reported in literature (Hagihara et al, Drug Metab. Pharmacokinet. 23 (6): 4.12-420 (2008) & Proceedings of the 54th ASMS Conference on Mass Spectrometry and Allied Topics, 2008). Use of the active metabolite as a therapeutic compound is not proposed in literature for none of the thienopyridine derivatives due to its transient & highly reactive character. Three different isomers are expected from the oxidation of clopidogrel at 2-position, all may be interchangeable to each other, which are as follows:

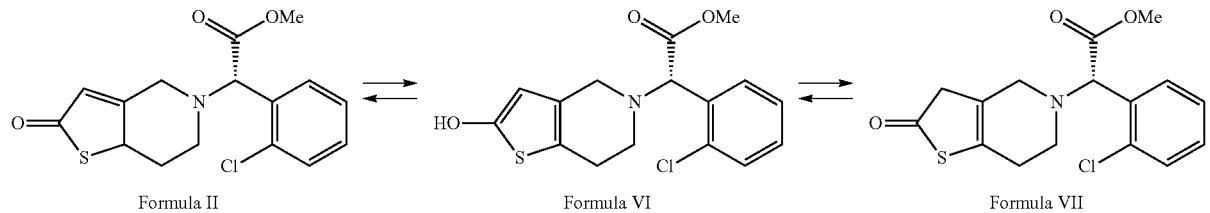 [SMILES: COC(=O)[C@H](c1ccccc1Cl)N1CCC2SC(=O)C=C2C1 ; COC(=O)[C@H](c1ccccc1Cl)N1CCc2sc(O)cc2C1 ; COC(=O)[C@H](c1ccccc1Cl)N1CCC2=C(CC(=O)S2)C1]

When 2-oxo-clopidogrel takes the structural formula it generates one additional chiral centre at position 7a and thus making it possible to exist in 2 different chiral isomers. However, due to aromatic nature of thieno-ring in Formula VI and associated transient conversion and dynamic equilibration of the keto-enol form of compound between structure II, VI and VII, the chiral centre will get disrupted and racemization of 2-oxoclopidogrel at 7a position is expected, which will result compound of formula II to exists as mixture of isomers. It has been shown that during administration of clopidogrel, both the isomers of the active metabolite are generated, implying that the intermediate oxo-metabolite is present as mixture of stereo-isomers in almost equal proportions (Thromb Haemost 2011; 1105: 696-705).

Further, the prasugrel metabolic pathway is elaborated in detail in literature (ref: Farid et al, Drug metabolism and disposition, 2007, vol. 35, p. 1096-1.104), which provides additional information on the possible metabolic pathways for the isomers of Formula II, VI, and VII, and revealed that the active metabolite generated from formula II only exhibits pharmacological activity.

Therefore there are unmet medical needs, which are not being offered by the current therapy options such as clopidogrel and prasugrel.

Therefore there is a need to provide improved medications or to improve clopidogrel to ameliorate its serious limitations, which include slow onset of action, high inter-individual variability, poor metabolizers status, dose ceiling effect, and also to improve the efficacy of clopidogrel, by increasing its inhibitory capacity on ADP induced platelet aggregation.

SUMMARY OF THE INVENTION

The present inventors have discovered that the use of clopidogrel presents substantial clinically significant limitations in inhibiting rapid platelet aggregation safely in a consistent manner for reasons as detailed above, though it is considered to be the gold standard among anti-platelet medicine available today. The invention, therefore, aims to provide new substances for treatment/prophylaxis of thrombosis and embolism, as well as compositions for use in such treatment, which ameliorate at least one dine clinical drawbacks of clopidogrel discussed above.

Surprisingly, it, has now been proven possible to resolve single active isomer of 2-oxo-clopidogrel substantially free of the counter isomer in a stereo-selective way from a mixture of isomers. Contrary to the belief, the highly active isomer of clopidogrel active metabolite has been generated from 2-oxo-clopidogrel, which has (7aS,2'S)-configuration, according to assignment of groups at their respective positions (according to numbering as shown in scheme 1 Formula II). The superior activity is confirmed by preclinical pharmacological evaluation. To our surprise, the isolated isomer remains stable and does not convert into (7aR,2'S)— isomer under normal conditions, through keto-enol tautomerism and/or equilibration.

The compound of the present invention shows only insignificant conversion into the mixture of isomers under normal conditions even in solutions.

Thus in an aspect, the present invention provides isomerically enriched & substantially pure isolated (7aS,2'S)-2-oxo-clopidogrel {chemical Name: Methyl (7aS,2'S)-2-(2-chlorophenyl)-2-(2,4,5,6,7,7a-hexahydrothieno[3,2-c]-5-pyridin-2-one)acetate} and its pharmaceutically acceptable salts for pharmaceutical application. The compound of the present invention is substantially stable to manufacture in substantially pure state and also, for the manufacture of drug products (formulations) for long term storage and pharmaceutical use. The compound of the present invention is substantially free of other isomers for example, compound of Formula VI, and Formula VII, apart from isomer of Formula IIB. Substantially free herein means the levels of these compounds individually or cumulatively are less than 10%, preferably less than, 5%, more preferably less than 3%, still more preferably, less than 1.0%.

In another aspect, the present invention includes a new method of synthesizing substantially pure isomer of (7aS, 2'S)-2-oxoclopidogrel from a mixture of isomers obtained by a chiral selective synthesis comprising treating said mixture of isomers with an acid like sulphuric acid, sulphonic acids such as methane sulphonic acid, benzene sulphonic acid etc., and selectively crystallizing the compound of the present invention. The crystallization of the (7aS,2'S)-isomer may be carried out with sequential or simultaneous conversion of the (7aR,2'S)-isomer or without the transformation of the unwanted (7aR,2'S)-isomer. The isomer is produced with fully conservation of stereoconfiguration in solid form. The selectively precipitated salt may be used as such for pharmaceutical preparations or may be neutralized with suitable base to obtain the isomerically pure compound in free form.

In yet another embodiment of the invention, the mixture of (7aS,2'S)/(7aR,2'S) isomers may be treated in a polar organic solvent(s), and allowed to selectively crystallize pure (7aS, 2'S)-isomer, by optional seeding of crystals of pure isomer, and isolating crystalline compound as pure isomer. The crystallization of the (7aS,2'S)-isomer be carried with sequential or simultaneous conversion of the (7aR,2'S)-isomer or without the transformation of the unwanted isomer. In this process, (7aS,2'S)-2-oxoclopidogrel is isolated in, substantially pure form in its free base form, which may be converted to a pharmaceutically acceptable salt by treating with a suitable acid.

The invention also provides a method of treatment and/or prophylaxis of thrombosis and/or embolisms in a patient in need of such treatment, comprising administering an amount of isolated (7aS,2'S)-2-oxo-clopidogrel or a pharmaceutically acceptable salt thereof, while avoiding and/or alleviating the side effects associated with the clopidogrel acid metabolite of Formula IV, Formula VI, or VII which otherwise was impossible without the advent of the compound of the present invention.

In preferred embodiments of this aspect of the present invention, the method achieves a therapeutic effect substantially greater to that observed following the administration of a substantially higher dose of clopidogrel due to the elimination of unwanted metabolic products and other isomers in the administration of clopidogrel.

In preferred embodiments of this aspect of the present invention, the method results in the in vivo formation of the active metabolite of clopidogrel at a concentration greater than or equivalent that observed following administration, of a substantially higher dose of clopidogrel.

In all aspects of the present invention, the onset of therapeutic action upon administration of isolated substantially pure (7aS,2'S)-2-oxoclopidogrel is at least 50% more rapid than that observed following administration of a substantially higher dose of clopidogrel.

Further, in all aspects of the present invention, various amounts of the isolated (7aS,2'S)-2-oxoclopidogrel, or a pharmaceutically acceptable salt thereof, may be administered. For example, the amount administered may be 20 to 40 mg and the substantially higher dose of clopidogrel may be 300 mg. Alternatively; the amount of substantially pure (7aS, 2'S)-2-oxoclopidogrel or a salt thereof may be 35 to 80 mg and wherein the equivalent substantially higher close of clopidogrel may be 600 mg. In alternative embodiments, the amount of substantially pure (7aS,2'S)-2-oxoclopidogrel or a salt thereof may be 50 to 100 mg and the substantially higher dose of clopidogrel may be 900 mg. In still, further embodiments, the amount of substantially pure: isolated (7aS,2'S)-2-oxoclopidogrel or a salt thereof may be 3 to 15 mg and the substantially higher dose of clopidogrel may be 75 mg. Alternatively, the amount of substantially pure (7aS,2'S)-2-oxoclopidogrel, or a salt thereof may be 6 to 20 mg and the substantially higher dose of clopidogrel may be 150 mg. It should be understood that different salts of compound of the formula may have different molecular weights and therefore for the purposes of dose calculation, it is based on the amount of non-salt form of the compound (i.e. base).

As an alternative to therapy involving the administration of a series of repeated closes to a patient, a higher loading dose may be followed by one or more maintenance doses. For example, a loading dose of 20-60 mg substantially pure (7aS, 2'S)-2-oxoclopidogrel or a salt thereof may be administered to a patient resulting in greater than 50% inhibition of ADP induced human, blood aggregation in most patient population. In certain embodiments of the present invention, this, or an alternative loading dose may be followed with a maintenance dose of 3-15 mg substantially pure (7aS,2'S)-2-oxoclopidogrel or a salt thereof, is administered to a patient, resulting in greater than 50% inhibition of ADP induced human blood platelet aggregation.

According to a fourth aspect of the present invention, there is provided a method for minimizing inter individual platelet reactivity variability and metabolic loading in the treatment and or prophylaxis of thrombosis and/or embolisms observed following administration of a dose of clopidogrel said method comprising administering substantially pure (7aS,2'S)-2-oxoclopidogrel or its pharmaceutically acceptable salt to a patient in need thereof.

The inter-individual variability may be due to CYP450 isoforms and its polymorphic manifestations, for example, in the CYP2C 19*2 allele or CYP2C19*17 allele. Additionally or alternatively, the inter-individual variability may be due to P-glycoprotein efflux transports.

According to a fifth aspect of the present invention, there is provided a method for the treatment or prophylaxis of thrombosis or embolisms comprising administration of a substantially pure (7aS,2'S)-oxo-clopidogrel or a pharmaceutically acceptable salt and a proton pump inhibitor.

In all aspects of the present invention, the methods discussed herein may additionally comprise the step of administration of one or more additional therapeutic agents. These may include, for example, anti-platelet agents selected from aspirin, cilostazol and dipyridamole. These additional agents may be administered simultaneously, sequentially or subsequently or in combination to the principal active ingredient.

According to a sixth aspect of the present invention, there are provided compositions for use in the methods described herein. For the avoidance of any doubt, where reference is made to the administration of an amount of active ingredient as a substantially pure (7aS,2'S)-oxo-clopidogrel or a pharmaceutically acceptable salt, this may be comprised within the composition of this aspect of the invention.

According to a seventh aspect of the present invention, there is provided a fixed dose composition of a substantially pure (7aS,2'S)-oxo-clopidogrel or a pharmaceutically acceptable salt characterized in that said composition comprises a dose of 1 to 60 mg of substantially pure isomer of 2-oxoclopidogrel or a salt thereof.

In a preferred aspect of the present invention, the fixed dose composition comprises a dose of a substantially pure (7aS, 2'S)-oxo-clopidogrel or a pharmaceutically acceptable salt thereof of 5-30 mg. The fixed dose composition may additionally or alternatively further comprise one or more anti-platelet agents selected from aspirin, cilostazol and dipyridamole.

The advantages of the present invention are realized through use of substantially pure isolated (7aS,2'S)-2-oxoclopidogrel or a salt thereof, which in turn is substantially free of isomer of formula IIB.

Structure:

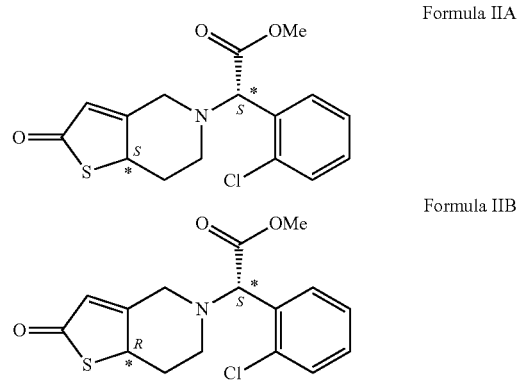

Formula IIA

Formula IIB

DETAILED DESCRIPTION OF THE INVENTION

Figure 1:
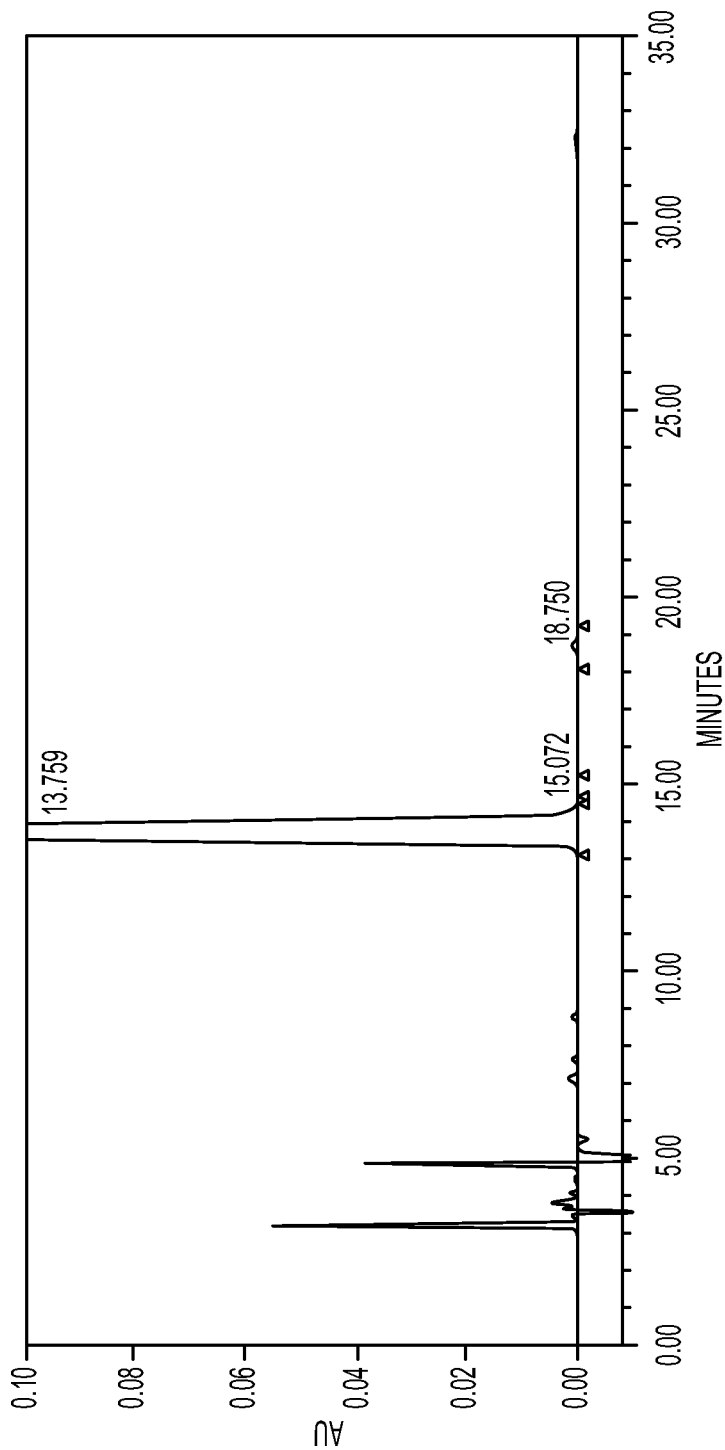
FIG. 1. A representative HPLC chromatogram of (7aS, 2'S)-oxo-clopidogrel bisulphate run on Chiralpak AD-H column.

Unless specified otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described. To describe the invention, certain terms are defined herein specifically as follows.

Unless stated to the contrary, any of the words "including;" "includes," "comprising," and "comprises" mean "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth the appended claims.

It has now surprisingly been found that it is possible to isolate a substantially pure (7aS,2'S)-2-oxo-clopidogrel (Formula IIA) or as a pharmaceutically acceptable salt, which can be administered to human to obtain a higher inhibition of ADP induced platelet aggregation with faster onset, which will ameliorate one or more of the drawbacks of clopidogrel. The present invention meets the long felt need in the treatment of thrombosis and embolism and associated disease conditions. The various aspects of the invention are described in detail with specific embodiments/conditions hereafter.

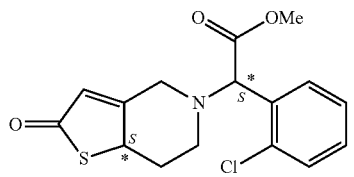

Formula IIA

Contrary to the belief, surprisingly, the present inventors could resolve single isomer of 2-oxo-clopidogrel substantially free of the counter stereo-isomer of Formula IIB, which can deliver active metabolite of desired absolute configuration more efficiently compared to mixture. The present invention is realized by way of preferential stereoselective crystallization of one of the isomer {(7aS,2'S)-isomer} from a mixture of isomers with or without dynamic conversion of counter stereo-isomer {(7aR,2'S)-isomer} through enol form. 2-oxo-clopidogrel can exists in three isomeric forms, namely structures of formula II, Formula VI and Formula VII. One of them can only generate additional chiral centre, thereby only one structural formula II exhibits chiral isomerism, and thus generate two chiral isomers, and most importantly only one of them can deliver the desired isomer of the clopidogrel active metabolite. Though compound of formula, VII gets metabolized to open the thiophene ring in vivo, interestingly, but none of them exhibits activity towards ADP receptor (Periello et al, Drug Metabolism & Disposition, 2002, page 1288-1295) and thus it is the isomer which can deliver the right clopidogrel metabolite is of pharmacological interest. Once the double bond in the ring flips between the tetrahydropyridine nucleus and the thiophene ring, it destroys the chiral centre at 7a position, especially during its formation, resulting in mixture of isomers. Therefore, to date, there are no reports available to exclusively isolate one of the isomer selectively. Contrary to the belief, it is now been possible to isolate exclusive isomer of structural formula IIA, surprisingly, the isolated isomer remain stable and resistant to conversion into mixture through keto-enol tautomerism and equilibration. The compound of the present invention shows only insignificant conversion into the mixture of isomers under normal conditions even in solutions. The compounds of the present invention are substantially free of other isomers for example, compound of Formula VI, and Formula VII, apart from isomer of Formula IIB. Substantially free herein means the levels of these compounds individually or cumulatively are less than 10%, preferably less than, 5%, more preferably less than 3%, still more preferably, less than 1.0%.

The present invention provides a method for synthesizing substantially pure (7aS,2'S)-2-oxoclopidogrel. The process comprises first synthesizing mixture of (7aS,2'S)/(7aR,2'S)-2-oxo-clopidogrel through a synthetic route disclosed in our co-pending application. The process according to the invention comprises reacting Methyl(R)-2-(4-nitrophenylsulfonyloxy)-2-(2-chlorophenyl)acetate with 5,6,7,7a-tetrahydro-4H-thieno[3,2-c]pyridin-2-one to form a mixture of isomers of compounds of formula IIA & IIB which may contains some amount of compounds of Formula VI and VII, and treating said mixture of isomers with an acid like sulphuric acid, sulphonic acids such as methane sulphonic acid, benzene sulphonic acid etc., and crystallizing the (7aS,2'S)-isomer selectively. Preferably the process is established with transformation of the (7aR,2'S)-isomer, so that the inactive isomer can be converted into the active compound and thus recovered for use. The isomer of the invention is produced with fully conservation of stereoconfiguration in solid form. The isomer of the present invention is characterized by its unique superior pharmacological activity. This process enables (7aS,2'S)-2-oxoclopidogrel to isolate directly in its acid salt form, which may be converted into a free base form under suitable reaction conditions. The process of isolation of compound of the present invention may be performed at appropriate temperature, preferably at a temperature, from 0 to +30° C.

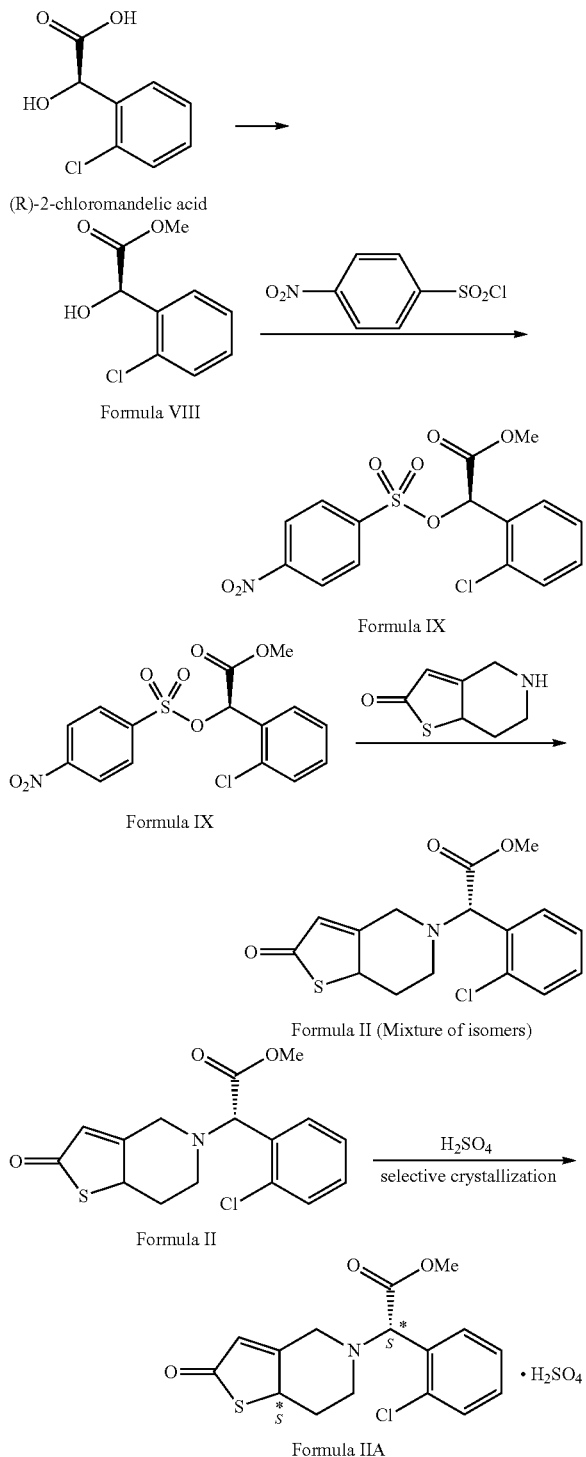

Scheme 2: synthesis of (7aS,2'S)-2-oxoclopidogrel conversion is effected in a suitable solvent. The solvent may be selected from organic solvents. Suitable solvents include, polar solvents like, C1-C4 alcohols, esters, and ketones. Exemplary C1-C4 alcohol include, methanol, ethanol, isopropanol, butanol etc. Exemplary ester solvents include, ethyl acetate, butyl acetate, propyl acetate, etc. Ketones include, but not limited to acetone, methyl ethyl ketone; and nitriles such as Acetonitrile.

In the process, according to the invention, a solution of 2-oxo-clopidogrel isomeric mixture is first obtained, and an acid of choice is added to the solution obtained. These steps may be performed under heating or cooling, appropriate for the reaction depending on the choice of solvent and acid used. Temperature of the reaction can range from cold to room temperature. The mixture may be maintained for suitable time, under suitable cooling for sufficient crystals to stereoselectively precipitates out. The crystallization process is carried out for sufficient period of time to allow complete conversion into the (7aS,2'S)-isomer, suitable for a period of 5 to 20 hours.

In an alternative embodiment of the invention, the mixture of (7aS,2'S)-/(7aR,2'S)-isomers may be treated in a polar organic solvent, and allowed to selectively crystallize the (7aS,2'S)-isomer enabling its isolation as pure isomer. The mixture may be optionally seeded with the substantially pure (7aS,2'S)-isomer free base to facilitate selective crystallization. The crystallization of the (7aS,2'S)-isomer may take place with sequential or simultaneous conversion of the (7aR, 2'S)-isomer or without the transformation of the unwanted (7aR,2'S)-isomer. Preferably the process is established with transformation of the (7aR,2'S)-isomer, so that the undesired isomer can be converted into the active compound and recovered for use in this process, (7aS,2'S)-2-oxoclopidogrel is isolated in substantially pure form in its free base form. The (7aS,2'S)-2-oxoclopidogrel base may be converted to its pharmaceutically acceptable salt by treatment with suitable acid in an appropriate solvent.

The isolation and stereo-selective conversion is effected in a suitable solvent. The solvent found useful are polar organic solvents. Suitable solvents include, Ethyl acetate, Alcohol such as methanol either separately or as mixture.

Product characterization and isomer quantification is performed using Chiral HPLC. The analytical Conditions are given below in Table 1:

TABLE 1

| Instrument | Waters Alliance |
|---|---|
| Column | Chiralpak AD-H(250 X 4.6 mm X 5 μ) |
| Mobile phase | n-Heptane:isopropanol:Diethylamine:Trifluoroacetic Acid (900:100:0.5:0.5) |
| Flow rate | 0.9 ml/min |
| Column Temperature | 25° C. |
| UV Detection | 220 nm |
| Injection volume | 10 μl |
| Run Time | 40 min |
| Sample preparation | Weight 4 mg sample in 10 ml volumetric flask. Add 2 ml ethanol and 5 ml mobile phase and sonicate to dissolve. Make up with mobile phase. (400 ppm) |
| Retention time | (7aS,2'S)-2-oxoclopidogrel-about 14 min<br>(7aR,2'S)-2-oxoclopidogrel-about 20 min |

Note: Inject freshly prepared sample for each analysis.

The isomer of the present invention is characterized by its unique pharmacological activity and further structural identification by NMR, and Chiral HPLC from rest of the isomers. It exhibits optical rotation characteristic from the mixture of isomers.

Figure 2:
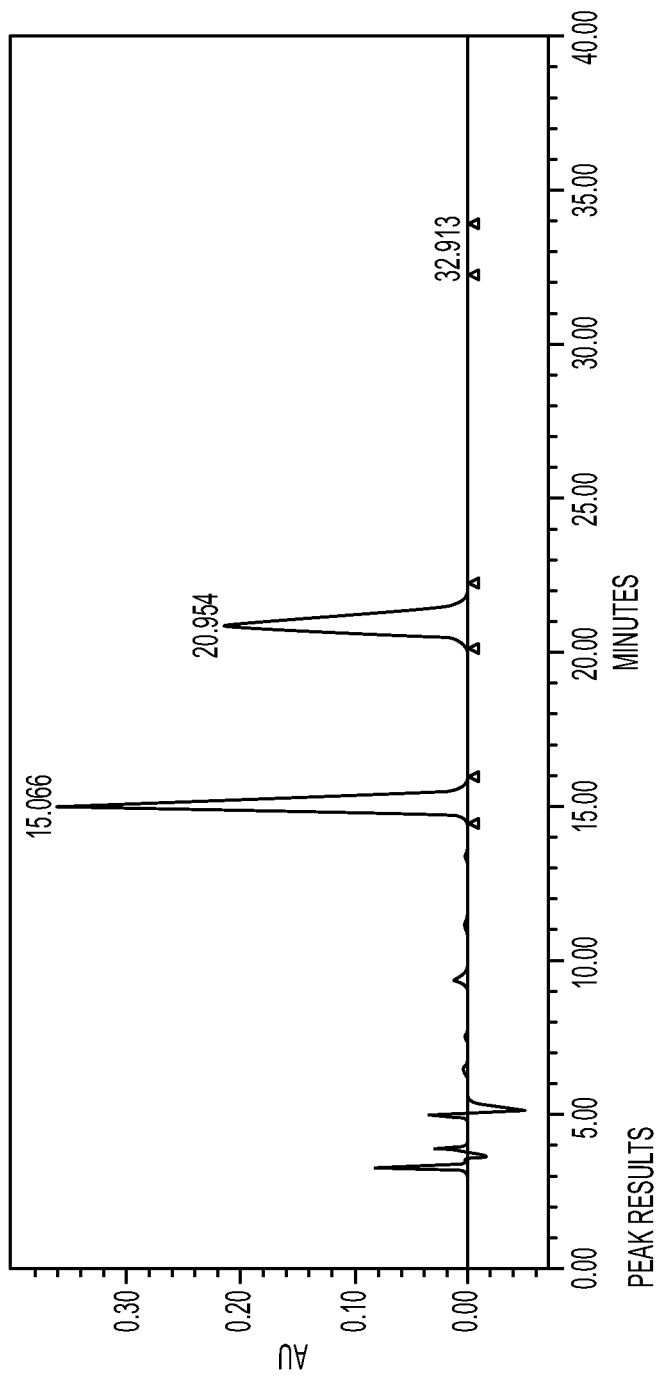
FIG. 2. A representative HPLC chromatogram of mixture of (7aS,2'S)/(7aR,2'S)-oxo-clopidogrel base run on Chiralpak AD-14 column.
Figure 3:
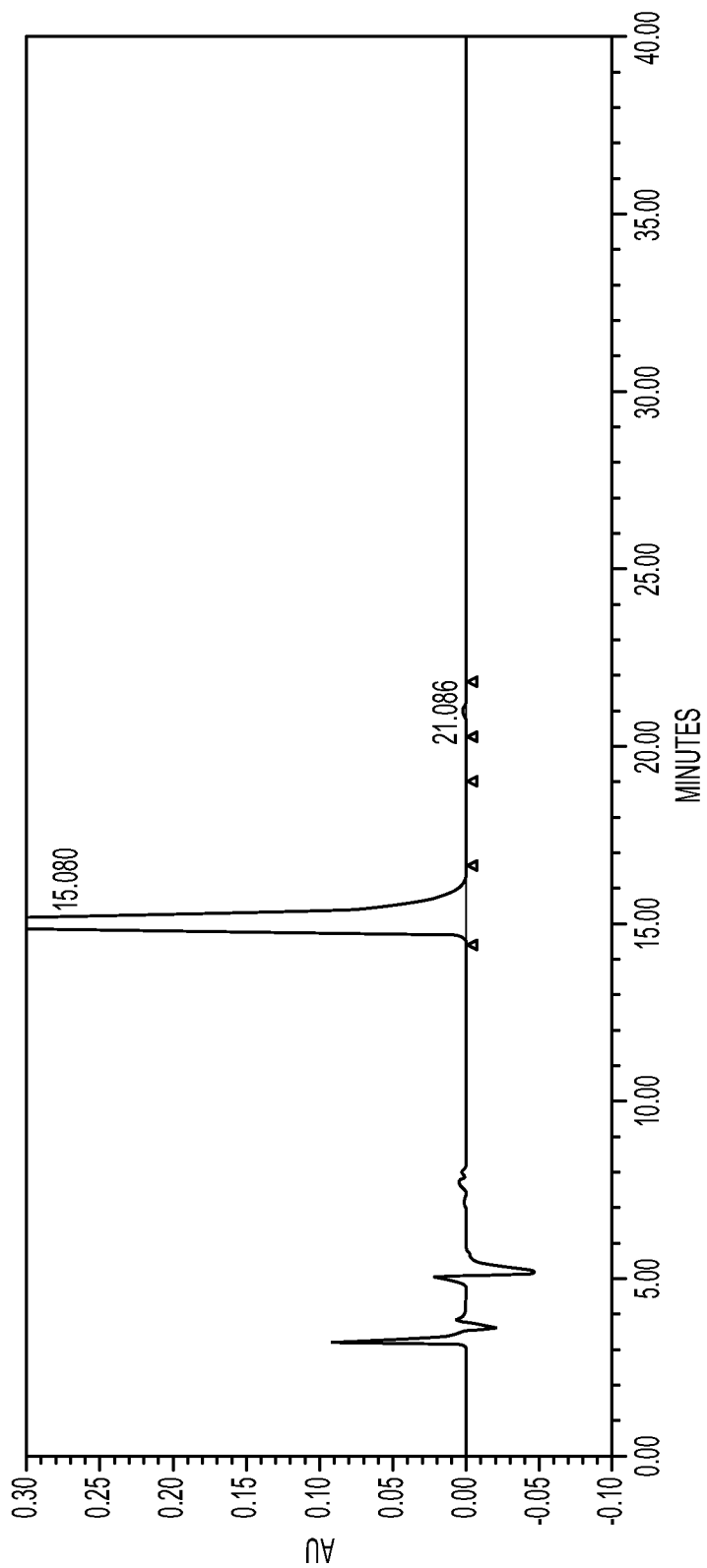
FIG. 3. A representative HPLC chromatogram of substantially pure ((7aS,2'S))-oxo-clopidogrel free base run on Chiralpak AD-H column.
Figure 4:
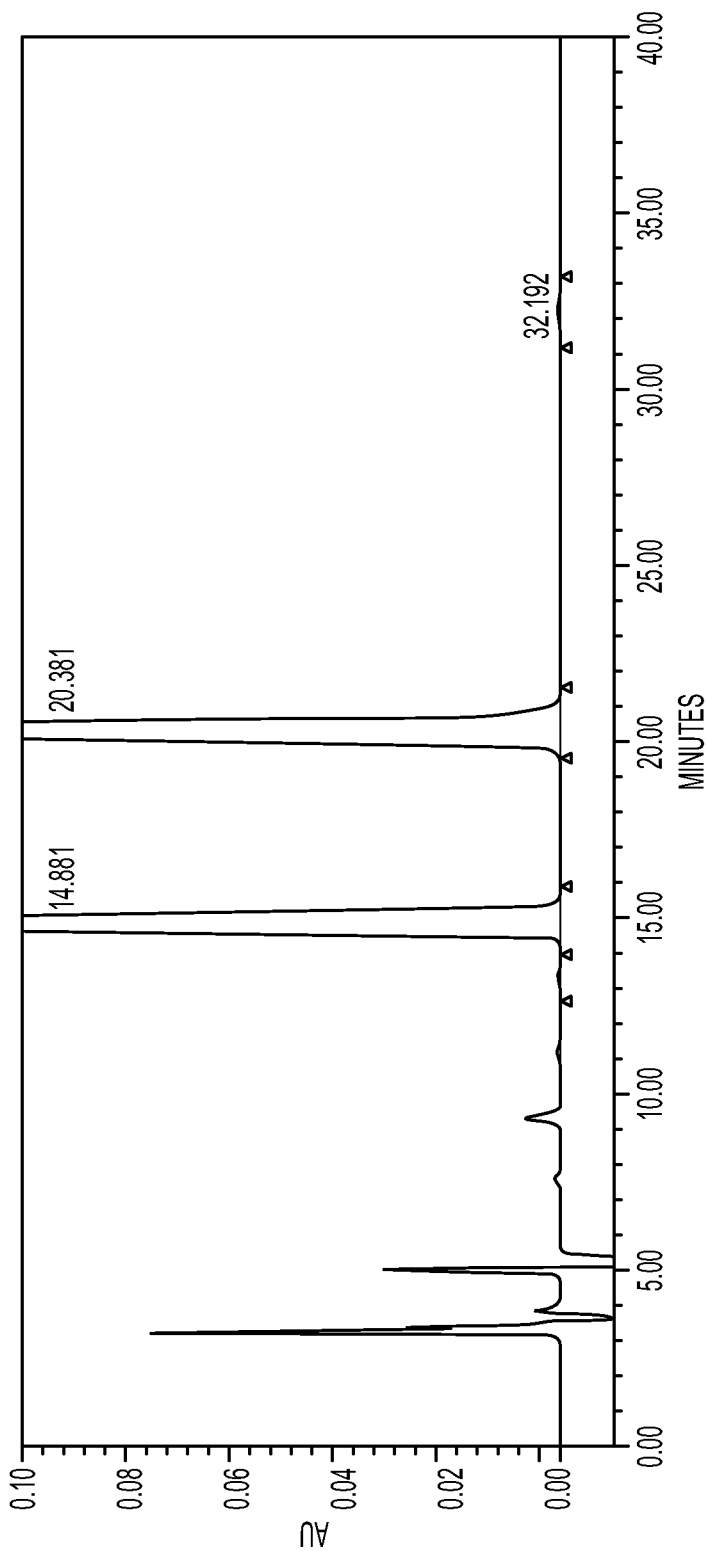
FIG. 4. A representative HPLC chromatogram of (7aS, 2'S)/(7aR,2'S)-oxo-clopidogrel hydrochloride run on Chiralpak. AD-H column.
Figure 5:
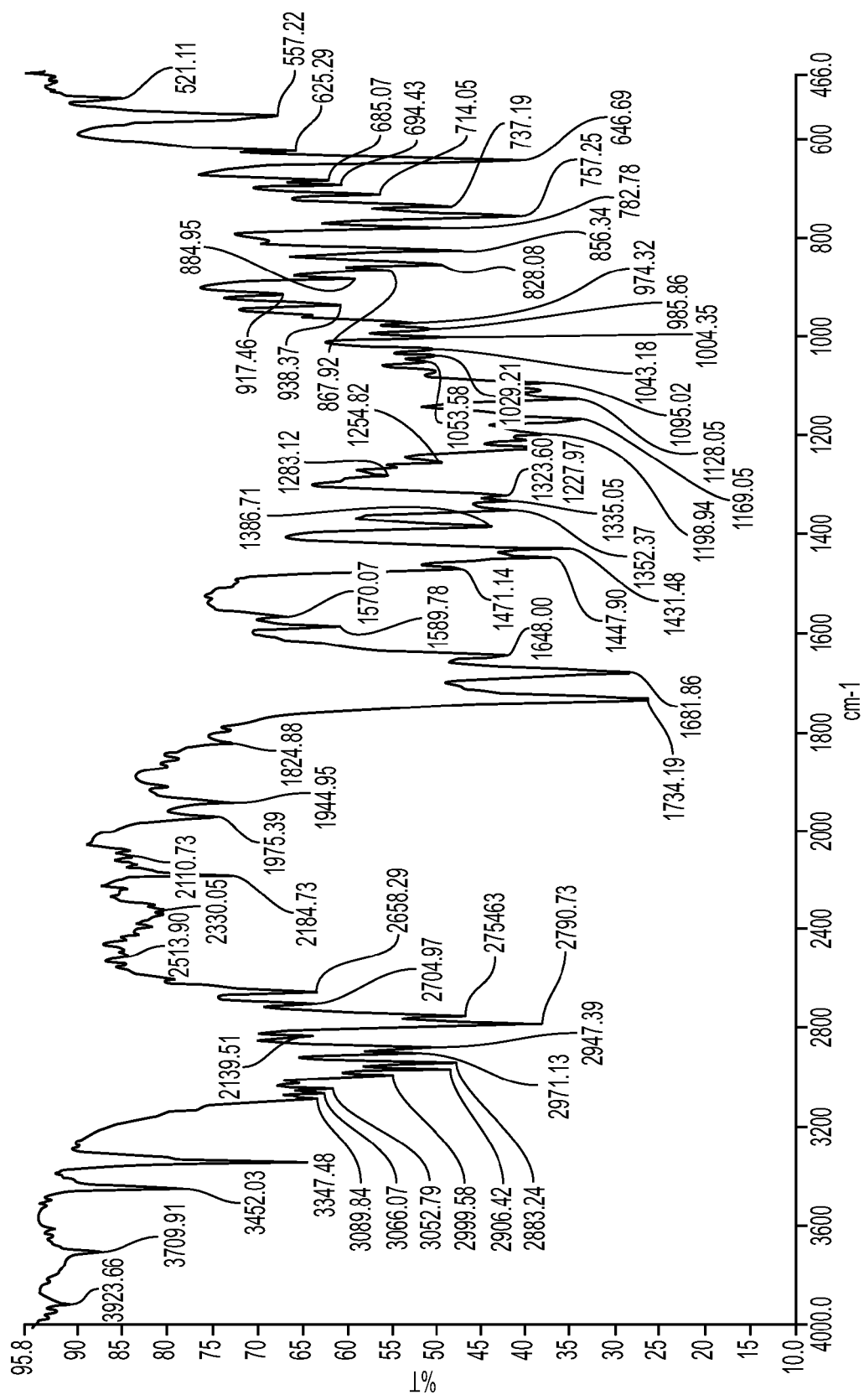
FIG. 5. A representative IR spectra of (7aS,2'S)-oxo-clopidogrel free base.
Figure 6:
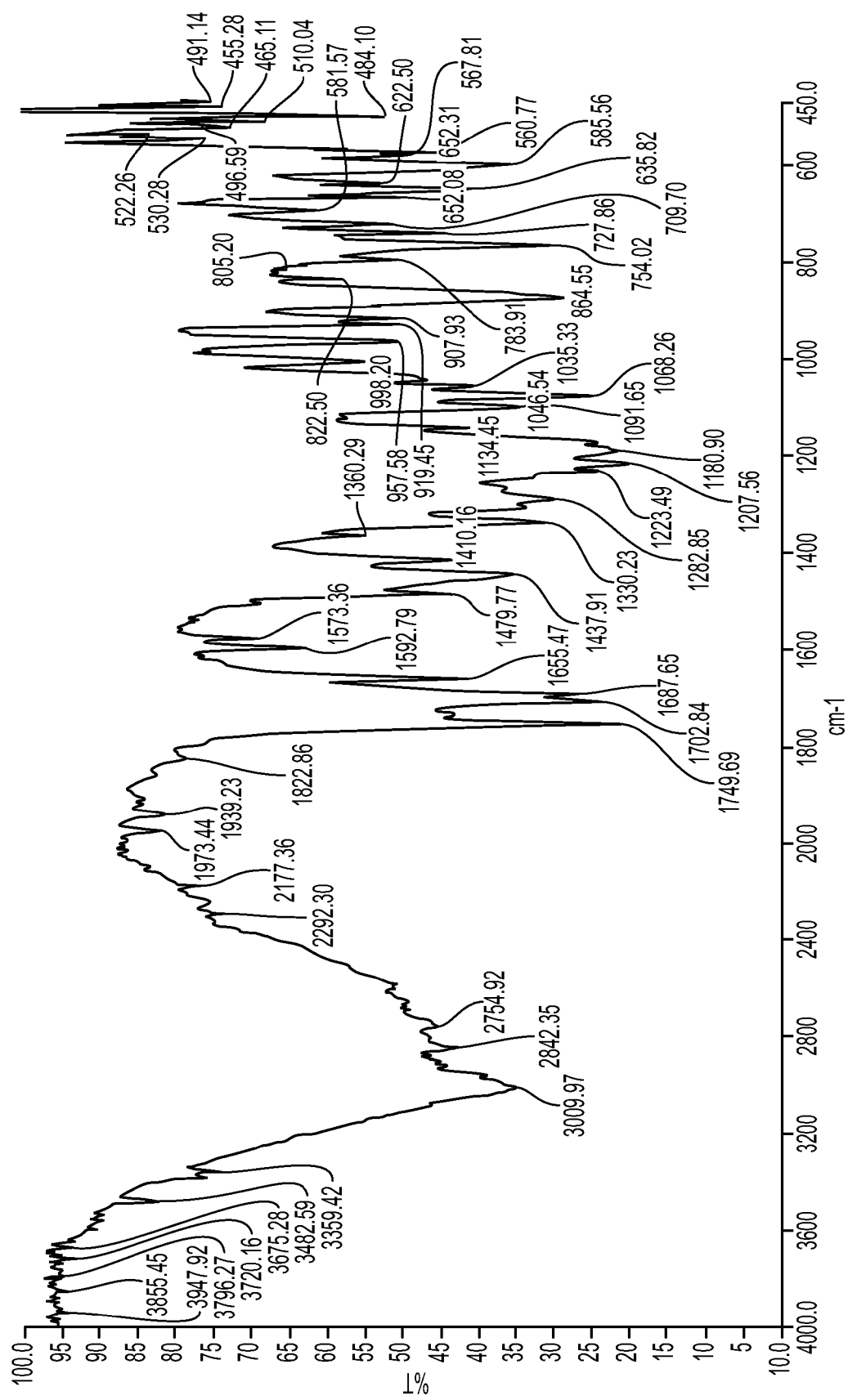
FIG. 6. A representative IR spectra of (7aS,2'S)-oxo-clopidogrel bisulphate.
Figure 7:
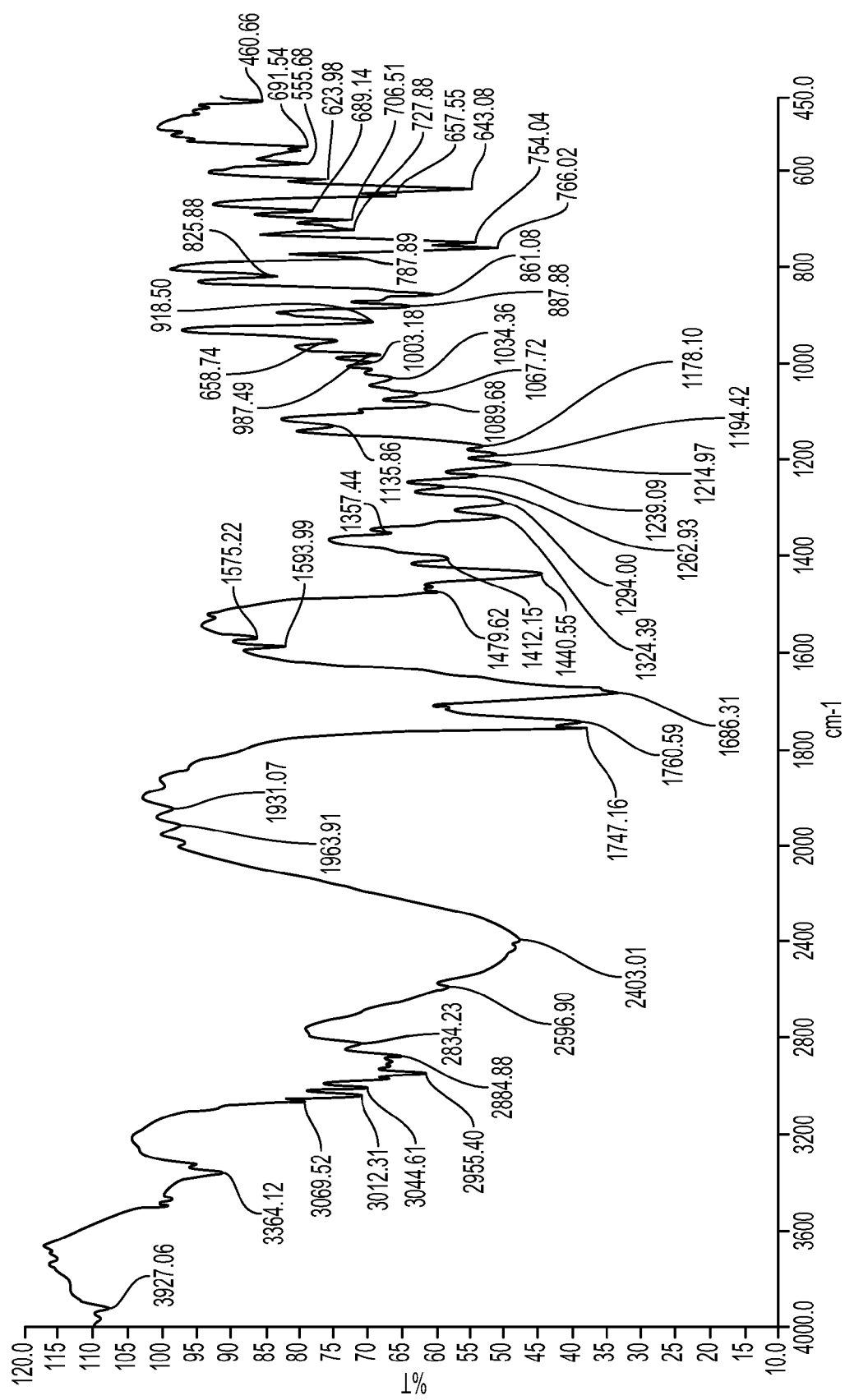
FIG. 7. A representative IR spectra of (7aS,2'S)/(7aR,2'S)-oxo-clopidogrel hydrochloride.

The acid is preferably selected from acids such as sulphuric acid or sulphonic acid, for example methane sulphonic acid, benzene sulphonic acid etc. The isolation and stereo-selective A typical HPLC chromatogram of pure isomer and mixture of isomers are presented in FIG. 1-2.

The X-Ray powder pattern, IR spectra and DSC data are presented in FIGS. 5 to 11.

The compound of Formula II is an intermediate metabolite of clopidogrel. Despite the structure or this metabolite and its position in the metabolic pathway of clopidogrel being known for almost 20 years, its use as an active agent for the treatment of thrombosis and/or embolisms has not previously been suggested. This is partly because this metabolite and the one identified as Formula IV in the metabolic pathway mentioned herein before has been found to be inactive. Moreover, the existence of single isomer was not possible without the advent of the present invention because of the isomeric nature of the oxo-clopidogrel, and its conversion into isomeric mixture of isomers of Formula IIB, VI, and VII.

The inventors have now been able to produce a substantially pure (7aS,2'S)-oxo-clopidogrel or a pharmaceutically acceptable salt that can advantageously be administered directly to patients in place of clopidogrel and that this ameliorates sortie if not all of the disadvantages associated with the use of clopidogrel. By administering the compound of Formula II in its substantially pure (7aS,2'S)-oxo-clopidogrel to a patient produces lesser number of the inactive metabolites in vivo. Further, it not only less one CYP mediated step to convert the compound of Formula II (as opposed to clopidogrel) to the active metabolite, hut also the metabolic load on CYPs in the production of inactive clopidogrel metabolites. Thus, the CYP's influence on the patient's ability to metabolize clopidogrel has on efficacy is effectively reduced.

The invention provides a method for treatment and/or prophylaxis of thrombosis and/or embolism, where the method comprises administering a predetermined dose of an isolated substantially pure (7aS,2'S)-2-oxo-clopidogrel (Formula IIA) or a pharmaceutically acceptable salt thereof such that it results in the in-vivo formation of the active metabolite of clopidogrel at a concentration equivalent or greater than that achieved through the administration of a substantially greater dose of clopidogrel. In a preferred embodiment, the present invention enables a substantial reduction in the dose of active ingredient required for achieving a therapeutic concentration of active metabolite of clopidogrel compared with administration of conventional therapeutic doses of clopidogrel. Thus, dose tolerability and efficacy are enhanced significantly.

Present invention not only improve the onset of therapeutic action by achieving greater than 50% inhibition of ADP induced platelet aggregation in shorter period and reduces inter individual variability, but also eliminates the side effects associated with the inactive metabolites (for example, Formula IV) and reduces the metabolic load on liver.

In aspects of the present invention, one or more additional active compounds may be administered including anti-platelet agents like aspirin, cilostazol, dipyridamole and the like. The antiplatelet agents may operate by a mechanism, similar or different to the clopidogrel active metabolite to achieve desired levels of anti-platelet activity. The second or subsequent anti-platelet agent may be administered separately, sequentially or simultaneously with a substantially pure (7aS, 2'S)-2-oxo-clopidogrel or a pharmaceutically acceptable salt thereof.

In aspects of the present invention, a dose ranging from 20-100 mg of a substantially pure (7aS,2'S)-2-oxo-clopidogrel or a pharmaceutically acceptable salt be administered as an initial loading dose, and if necessary, a maintenance dose as low as 3-20 mg may subsequently be administered such that the systemic concentration of active, metabolite is equal or greater than that amount obtained by administering a loading dose of 300-900 mg and a maintenance dose off 75-150 mg of clopidogrel, respectively. More preferably the loading dose of the present invention is between 20-80 mg and maintenance dose is between 5-15 mg. Still further lower doses may be administered, if the desired inhibition is equivalent or slightly inferior to that provided by clopidogrel. The above doses are calculated for human of average body weight of 60 kgs. Dose adjustments may be necessary according to body weight of patients, severity of disease, genetic polymorphism of CYPs, at the discretion of the practitioner for the target platelet inhibition.

In aspects of the present invention, there are provided compositions for use in the methods discussed herein. For example, the present invention provides a fixed dose pharmaceutical composition comprising 1 mg to 60 mg of an isolated substantially pure (7aS,2'S)-2-oxo-clopidogrel or a pharmaceutically acceptable salt thereof and optionally one more pharmaceutically acceptable excipients. The fixed dose combination of the present invention may be administered along with one or more active compounds including antiplatelet/ cardiovascular agent like aspirin, cilostazol etc. which may operate by a mechanism similar or other than clopidogrel active metabolite.

The inventive selection of the compounds of Formula IIA significantly contributes to improvements in the antiplatelet treatment compared to the use of clopidogrel and improves its therapeutic efficiency by about 5-10 times or more as well as reducing the associated toxicity/side effects or metabolic load associated with clopidogrel treatment.

The present invention can provide a therapeutically effective concentration of desired active metabolite isomer of clopidogrel in a short time after administration, which not only improves the onset of action but also achieves greater than 50% inhibition of ADP induced platelet aggregation. The onset of action can be (as measured by 50% inhibition of ADP induced platelet aggregation) achieved in less than 1 hour, more preferably in 30 minutes, compared to 4-6 hours for clopidogrel. Irrespective of the dose of compounds of Formula IIA, the maximum platelet aggregation can be achieved in less than 1 hour after oral administration. This invention also ameliorates the dose ceiling effect observed with higher doses of clopidogrel and provides significantly higher active metabolite output and reduced metabolic loading in liver. Furthermore, as clopidogrel is a P-Glycoprotein (Pgp) substrate, its absorption is influenced by Pgp inhibitors or inducers, which are likely to alter the clinical effects of clopidogrel. This effect should also be reduced to a large extent by the administration of the compositions of the present invention. Additionally, the invention may permit the use of proton pump inhibitors in combination with Formula IIA. It is believed that this is because the role of CYP2C19 (which plays a significant part in the metabolism of clopidogrel) is reduced substantially with the use of the compositions and methods of the present invention, PPI's being inhibitors of CYP2C19.

Apart from increasing the active metabolite concentration and achieving greater platelet inhibitory activity, the compositions and methods of the present invention may reduce the toxicity and I or associated side effects observed due to the formation of clopidogrel acid (Formula IV) following clopidogrel administration. The lethal dose of clopidogrel is about 5000 mg per kg in rat and 90% of clopidogrel is converted to clopidogrel acid in vivo. Thus, it appears that around 90% of the toxicity of clopidogrel may be related to the clopidogrel acid metabolite (Formula IV). Given that the compositions and methods of the present invention advantageously enable the amount of active ingredient administered to patients to be reduced, while also eliminating the formation of clopidogrel acid metabolite etc., following administration, the associated toxicity or adverse side effects will be reduced by at least 9-10 times compared to current: clopidogrel therapeutic use.

The compounds employed in the compositions and methods according to present invention are preferably present in the form of their pharmaceutically acceptable salts. Examples of such acid addition salts include salts with mineral acids, especially hydrohalic acids (such as hydrofluoric acid, hydrobromic acid, hydroiodic acid or hydrochloric acid), nitric acid, carbonic acid, sulfuric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; and salts with organic carboxylic acids, such as acetic acid, propionic acid, butyric acid, fumaric acid, tartaric acid, oxalic acid, malonic acid, maleic acid, inane acid, succinic acid, benzoic acid, mandelic acid, ascorbic acid, lactic acid, gluconic acid or citric acid. Salts, which are not pharmaceutically acceptable may be employed in the manufacture of the compounds employed in the methods and compositions according to the invention. Preferred salts are hydrogen sulphate (bisulphate) and benzene sulphonate.

The methods and compositions of the present invention, may further employ one or more active compounds including cardiovascular or anti-platelet agents such as aspirin, cilostazol, dipyridamole and the like which may operate by a mechanism similar or different to the clopidogrel active metabolite to achieve desired levels of anti-platelet activity. The second or subsequent anti-platelet agent may be administered separately, simultaneously or subsequently with the compound of Formula IIA or as a pharmaceutically acceptable salt thereof. The present invention encompasses such modifications thereof for achieving desired goal of inhibition of platelet aggregation.

In other aspects, the present invention provides a fixed dose pharmaceutical composition of compound of Formula IIA a pharmaceutically acceptable salts thereof wherein the dose of said compound of Formula IIA is selected from the range of 1 mg to 60 mg and the composition optionally comprises pharmaceutically acceptable excipients. The fixed dose composition of the present invention may comprise or be administered along with one or more active compounds including antiplatelet/cardiovascular agents such as aspirin, cilostazol or the like which may operate by a mechanism similar or different to the clopidogrel active metabolite.

The fixed dose pharmaceutical compositions of the invention are preferably administered orally on a daily basis as an immediate release or modified release dosage form.

The dosage form may be formulated as a single unit dosage, as two separate unit dosages, and/or in any oldie many variations known in the art, which include, but are not limited to, tablets, pills, hard capsules, soft capsules, pharmaceutical sachets and powders for reconstitution.

The formulations of the invention may further contain water insoluble permeable polymers, herein defined as "modified release polymers", to adjust their release profile. These polymers may either be coated onto formulations such as tablets, microgranules, capsules or pills, or be mixed together with the other ingredients of any of the formulations listed above.

In one embodiment; the pharmaceutical compositions of the present invention are provided in the form of tablets prepared by mixing the active agents with excipients. Typical excipients include diluents, fillers, binders, lubricants, disintegrants, glidants, colorants, pigments, taste masking agents, modified release polymers, sweeteners, plasticizers, and any acceptable auxiliary substances such as absorption enhancers, penetration enhancers, surfactants, co-surfactants, and specialized oils. Examples of excipients include calcium phosphates, such as dibasic calcium phosphate, anhydrous dibasic calcium phosphate, tribasic calcium phosphate, etc.; microcrystalline cellulose, powdered cellulose; starch, pregelatinized starch; sodium starch glycolate; dextrates; mannitol, sorbitol; povidone; ethyl cellulose; lactose; kaolin; silicic acid; lubricants such as magnesium stearate, calcium stearate, stearic acid, mineral oil, glycerin, sodium lauryl sulfate, polyethylene glycol; and/or talc. Sodium starch glycolate, talc and the lubricant magnesium stearate may be used to prepare compositions of the present invention to aid in tablet manufacture. A premix of compound of Formula IIA may be obtained by mixing said compound with ingredients and thereafter either directly compressing the mixture into tablets or filling said mixture into capsules optionally along with other suitable ingredients to obtain final dosage form. A unit dose of the free form of a compound of Formula IIA may be obtained as a granular premix by suitably processing that compound with acceptable ingredients such as polymers, which can be directly compressed or formulated with additional excipients.

The compositions and methods of the present invention may be employed in the prevention and/or treatment of pathological states such as disorders of the cardiovascular and cerebrovascular system such as the thromboembolic disorders associated with atherosclerosis or with diabetes such as unstable angina, cerebral attack, restenosis following angioplasty, endarterectomy or fitting of metallic endovascular prostheses, with rethrombosis following thrombolysis, with infarction, with dementia of ischaemic origin, with peripheral arterial diseases, with haemodialyses, with auricular fibrillations or during the use of vascular prostheses or aortocoronary bypasses or in relation to stable or unstable angina.

The compounds of Formula II or its acid salts can be obtained by a method illustrated in the examples.

Preparation and pharmacological evaluation of compounds of Formula IIA is presented below:

Example 1

Preparation of mixture of (7aS,2'S)/(7aR,2'S)-isomers of 2-oxoclopidogrel a) Methyl-(R)-2-hydroxy-2-(2-chlorophenyl)acetate In a four necked round bottomed flask, 500 gm of (R)-2-chloromandelic acid was taken in 2600 ml methanol. Then 18.8 gm of sulfuric acid was added and heated to reflux, till completion of reaction. Then excess of methanol was distilled off under reduced pressure. Residue was taken in dichloromethane and washed with aqueous sodium bicarbonate solution. Dichloromethane was distilled under reduced pressure to obtain 522 gm of Methyl-(R)-2-hydroxy-2-(2-chlorophenyl)acetate as an oil. Yield: 94%. Purity: 98.5% b) Methyl(R)-2-(4-nitrophenylsulfonyloxy)-2(2-chlorophenyl)acetate

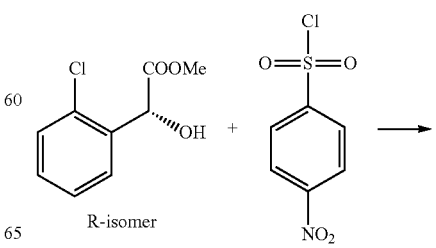

-continued

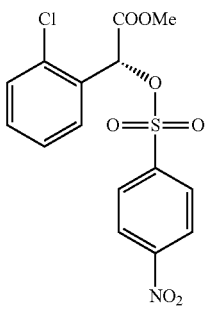

In a four necked round bottomed flask, under nitrogen atmosphere, 640 ml of dichloromethane, 221 gm of 4-Nitro benzene sulfonyl chloride, 12.1 gm of 4-dimethylaminopyridine, and 200 gm of Methyl(R)-2-hydroxy-2(2-chlorophenyl)acetate were added. It was cooled to around 0° C., and 101 gm of triethylamine was added. Mixture was stirred at about 0° C. till completion of reaction. The reaction mass was quenched in aqueous hydrochloric acid solution and extracted with dichloromethane. Dichloromethane layer was concentrated under reduced pressure.

Oily mass obtained after concentration, was then purified by crystallization in ethylacetate-hexane mixture, and dried under reduced pressure to get 281 gm Methyl(R)-2-(4-nitrophenylsulfonyloxy)-2(2-chlorophenyl)acetate. Yield: 73%, Purity: 93%.

c) Methyl (7aS,2'S)/(7aR,2'S)-2(2-chlorophenyl)-2-(2,4,5,6,7,7a-hexahydrothieno[3,2-c]-5-pyridin-2-one)acetate

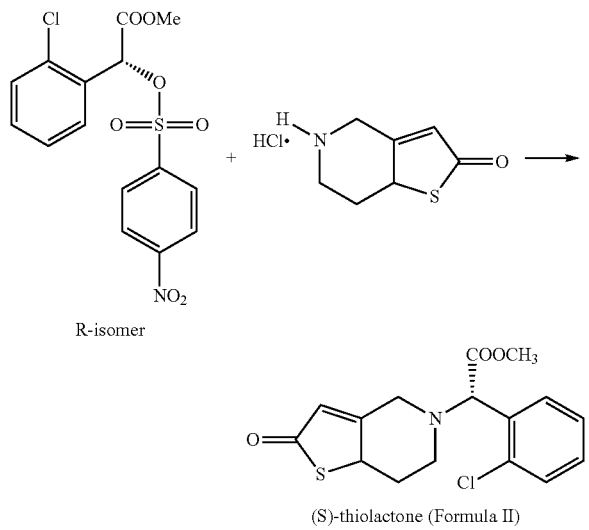

In a four necked round bottomed flask, under nitrogen atmosphere, 1000 ml acetonitrile, 49.5 gm of 5,6,7,7a-tetrahydro-4H-thieno[3,2-c]pyridin-2-one HCl, 55 gm of sodium carbonate and 100 gm of Methyl (7)-2-(4-nitrophenylsulfonyloxy)-2(2-chlorophenyl)acetate were added and the mixture was heated to about 50° C. After reaction, reaction mass was filtered, filtrate concentrated and concentrated mass was taken in dichloromethane, washed with water and concentrated under reduced pressure. The oily residue was treated with IPA.HCl solution in isopropanol (IPA) and filtered to obtain the mixture of isomers as hydrochloride salt. To it sodium bicarbonate solution was added till pH turned alkaline. The product was then extracted in dichloromethane (MDC). The MDC layer was washed with water, dried and distilled to obtain the product as an oily residue.

Ratio of (7aS,2'S)/(7aR,2'S)-isomers as per chiral HPLC: 53.62/46.38%.

Example 2

Methyl (7aS,2'S)-2-(2-chlorophenyl)-2-(2,4,5,6,7,7a-hexahydro thieno[3,2-c]-5-pyridin-2-one)acetate In a four necked round bottomed flask, under nitrogen atmosphere, 150 ml of ethyl acetate-methanol and 70 gm of mixture or isomers (Ratio of (7aS,2'S)/(7aR,2'S)-isomers=53.62:46.38) was taken and warmed to dissolve, and stirred for 20 hours under room temperature, crystals obtained were filtered and the solid was dried to obtain 52 gm Methyl (S)-2(2-chlorophenyl)-2-(2,4,5,6,7,7a-hexahydrothieno[3,2-c]-5-pyridin-2-one)acetate. Yield=60%, Ratio of (7aR,2'S)/(7aR,2'S)-isomers as per chiral HPLC: 99.5:0.5.

$^1$H-NMR (DMSO-$d_6$) spectra collected on a BRUKER 400 MHz instrument has shown values given in table 2 corresponding to structure of formula IIA free base below:

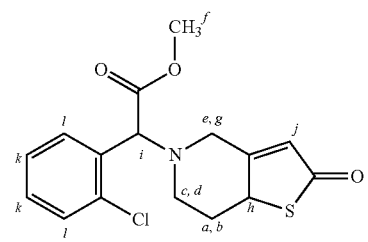 [SMILES: COC(=O)C(c1ccccc1Cl)N1CCC2SC(=O)C=C2C1]

TABLE 2

| Chemical shift value (δ/ppm) | Assignment (Multiplicity[#], Number of protons, Position*) |
|---|---|
| 1.54-1.64 | (m, 1H, a) |
| 2.36-2.41 | (m, 1H, b) |
| 2.56-2.62 | (m, 1H, c) |
| 2.92-2.96 | (d, 1H, d) |
| 3.21-3.24 | (dd, 1H, e) |
| 3.66 | (s, 3H, f) |
| 3.86-3.89 | (dd, 1H, g) |
| 4.48-4.52 | (m, 1H, h) |
| 4.87 | (s, 1H, i) |
| 6.21 | (s, 1H, j) |
| 7.37-7.41 | (m, 2H, k) |
| 7.49-7.52 | (m, 2H, l) |

[#]m—multiplet, s—singlet, d—doublet of doublet.

Single crystal analysis data of material conforms to (7aS,2'S)-configuration.

Example 3

Preparation of Methyl (7aS,2'S)-2-(2-chlorophenyl)-2-(2,4,5,6,7,7a-hexahydrothieno[3,2-c]-5-pyridin-2-one)acetate hydrogen sulfate In a four necked round bottomed flask, under nitrogen atmosphere, 1750 ml of acetone and 70 gm of Methyl(S)-2

(2-chlorophenyl)-2-(2,4,5,6,7,7a-hexahydrothieno[3,2-c]-5-pyridin-2-one)acetate isomeric mixture (Ratio of (7aS,2'S)/(7aR,2'S)-isomers=51.42:47.48) were added. It was cooled to around 5° C. and 20.8 gm of sulfuric acid was added slowly. After Sulfuric acid addition, stirred at about 20-30° C. temperature. Filtered and dried under reduced pressure to obtain 84 gm of Methyl (7aS,2'S)-2(2-chlorophenyl)-2(2,4,5,6,7,7a-hexahydrothieno pyridin-2-one)acetate hydrogen sulfate. Yield=93%; Purity by HPLC=99.5%, Ratio of isomers by Chiral HPLC=99.8:0.2.

$^1$H-NMR (DMSO-$d_6$) spectra collected on a BRUKER 400 MHz instrument has shown values given in table 3 corresponding to structure of formula IIA hydrogen sulphate below:

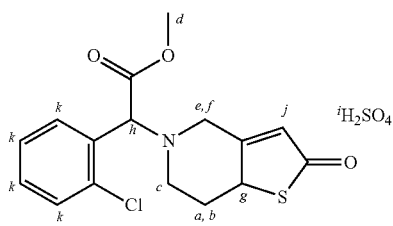

TABLE 3

| Chemical shift value (δ/ppm) | Assignment (Multiplicity[#], Number of protons, Position*) |
| --- | --- |
| 1.69-1.79 | (m, 1H, a) |
| 2.45-2.52 | (m, 1H, b) |
| 3.06-3.08 | (m, 2H, c) |
| 3.72 | (s, 3H, d) |
| 3.92-3.95 | (d, 1H, e) |
| 4.39-4.42 | (d, 1H, f) |
| 4.63-4.68 | (m, 1H, g) |
| 5.43 | (s, 1H, h) |
| 6.26 | (brs, 2H, i) |
| 6.45 | (s, 1H, j) |
| 7.46-7.60 | (m, 4H, k) |

[#]m—multiplet, s—singlet, d—doublet, brs—broad singlet.

Example 4

Preparation of Methyl(7aS,2'S)-2-(2-chlorophenyl)-2-(2,4,5,6,7,7a-hexahydrothieno[3,2-e]-5-pyridin-2-one)acetate benzene sulphonate 2.5 gm of Methyl(S)-2-(2-chlorophenyl)-2-(2,4,5,6,7,7a-hexahydrothieno[3,2-c]-5-pyridin-2-one)acetate (mixture of isomers) was taken in a round bottom flask. At about 50-60° C., IPA was added. Then 1.17 gm of benzenesulfonic acid was added. The title Product was allowed to crystallize out selectively, then cooled, maintained at room temperature, filtered and dried the crystals under vacuum to get 3.2 gm of the product.

Pharmacology and Toxicology

The pharmacological and toxicological results which are reported below demonstrate the properties of the compositions of the invention both from the point of view of toxicity and tolerance, and from the point of view of their activities, particularly inhibition of platelet and thrombotic aggregation.

Toxicological Study

The compositions of the invention demonstrate excellent tolerance and low toxicity. In addition, the tests carried out on the acute, chronic, subchronic and delayed toxicities in different species of animals, have not demonstrated any local or general reaction, disturbance or anomaly in the biochemical, macroscopic or microscopic examinations carried out during these experiments.

Pharmacological Study

The platelet aggregation inhibiting activity and the toxicity of the inventive compositions were compared to those of the clopidogrel as per standard procedures reported in literature (Cardinal, D. C. and Flower, (1980) *J. Pharm. Meth*. Vol. 3, pp: 135-158; Ingerman-Wojenski et al. (1983) *Thromb. Haemost*. Vol. 51, pp: 154-156).

The platelet aggregation inhibiting activities and the antithrombotic activities of the compounds were studied in the rats by standard methods.

1. Measurement of Platelet Aggregation with ADP

The activity on the aggregation of plates induced by ADP or collagen was determined ex-vivo.

The products as a suspension in 5% Gum Arabica (aq.) were administered by oral route to groups of six male rats of the SD strain, weighing 250-300 g. After 4 hours of the administration, 2 ml of blood is collected into the heparinized tubes by puncture of retro-orbital sinus. 0.5 ml of the anticoagulated blood is diluted with an equal volume of isotonic saline solution and incubated at 37° C. for 10 minutes. To the incubated whole blood, 10 µM ADP is added and the change in impedance (Ω), which reflects platelet aggregation, is recorded for 8 minutes with Chronolog Whole Blood Aggregometer (Model 592, Chrono-log Corp., USA). The percentage inhibition of platelet aggregation is calculated by the following formula considering the vehicle control reading as 100%:

$$\% \text{ Inhibition} = \frac{\text{Impedence } (\Omega) \text{ in vehicle control} - \text{Impedance } (\Omega) \text{ in test compound}}{\text{Impedance } (\Omega) \text{ in Vehicle Control}} \times 100$$

The results obtained for the aggregation with ADP are shown in Table 4; they demonstrate that activity of the molecule of Formula IIA, which is significantly superior to clopidogrel.

TABLE 4

| Product | Dose mg/kg | Qty of base administered | % aggregation* | % inhibition |
| --- | --- | --- | --- | --- |
| Control | | | | |
| Clopidogrel bisulphate | 25 mg/kg | 19.15 mg/kg | 22.85% | 77.15% |
| Prasugrel hydrochloride | 2.2 mg/kg | 2 mg/kg | 18.93% | 81.07% |
| (7aS,2'S)-2-oxoclopidogrel bisulphate | 3.5 mg/kg | 2.7 mg/kg | 9.14% | 90.86% |
| (7aS,2'S)-2-oxoclopidogrel bisulphate | 2.5 mg/kg | 1.9 mg/kg | 14.57% | 85.43% |
| (2'S)-2-oxoclopidogrel hydrochloride (ratio of (7aS,2'S)/(7aR,2'S): 51.8:48.2) | 2.2 mg/kg | 1.98 mg/kg | 51.96% | 48.04% |

*Mean of results ± standard deviation

2. Anti-Thrombotic Activity

The antithrombotic activity has also been studied in $FeCl_3$ induced Arterial Thrombosis Model according to standard procedures reported by William A. Schumacher et al., 2007 (Journal of Pharmacology and Experimental Therapeutics, 322 (I): 369-377) and Takao Tanaka et al. 2000 (European Journal of Pharmacology, 401: 413-418).

The products were dissolved in DMSO (1 mg/ml) and diluted in PEG/Water (Ratio: DMSO:PEG:Water=5:50:45), and were administered by the per oral mute to groups of 8 male rats of the SD strain, weighing 250-300 g after overnight fast. 1 hour post dosing, rats were anesthetized with Ketamine (100 mg/kg; i.p.), Xylazine (10 mg/kg; i.p) and placed on a heating pad. After aseptic preparation of the tracheal and scapular region of the rats, a midline incision of the tracheal area was made and a blunt dissection was performed to expose the common carotid artery. Approximately 2 cm of the common carotid artery was freed from the connective tissues, jugular veins, and vagus nerve and a ~3 mm filter paper, briefly soaked in 30% $FeCl_3$ solution, was placed around the artery for 10 min. The artery was isolated after 15 mins of the removal of filter paper and the rat was euthanized. Thrombus developed was scraped out from the extracted artery and kept for drying for 24 hours. The wet and dry weight of thrombus was recorded and expressed as mg weight of thrombus per kg body weight. % inhibition of the thrombus formation is calculated using the formula:

$$\% \text{ Inhibition} = \frac{\text{Thrombus wt. of vehicle control} - \text{Thrombus wt. of test compound}}{\text{Thrombus weight of vehicle control}} \times 100$$

The results which are presented in Table 5 show that (7aS, 2'S)-2-oxoclopidogrel of Formula IIA is the active isomer of thiolactone metabolite and is superior to clopidogrel.

TABLE 5

| Group | Compound | Dose (mg/kg); p.o. | Qty. of base administered (mg/kg) | Dry weight of Thrombus (mg/kg) (Mean ± SEM) | % Inhibition of Thrombus Formation (Mean ± SEM) |
|---|---|---|---|---|---|
| 1. | $FeCl_3$ Control (30%) | | | 4.05 ± 0.5 | |
| 2. | Clopidogrel bisulphate | 4 mg/kg | 3.06 mg/kg | 1.10 ± 0.2 | 73 ± 5.3% |
| 3. | (7aS,2'S)-2-oxoclopidogrel bisulphate | 1.3 mg/kg | 1.17 mg/kg | 0.98 ± 0.1 | 76 ± 3.3% |

*Mean of results ± standard deviation

We claim:

1. A solid form of substantially pure compound of formula IIA, wherein asterisks denote chiral carbon centers having a (S,S) absolute stereochemical configuration:

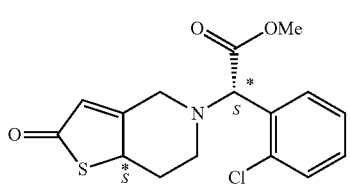

Formula IIA and wherein said compound exhibits an X-ray powder diffraction pattern comprising peak reflections in a range starting at 22.22 and ending at 22.8 degrees 2θ; a range starting at 23.0 and ending at 23.6 degrees 2θ; and a range starting at 26.8 and ending at 27.2 degrees 2θ.

2. A solid form of substantially pure compound of formula IIA, wherein the asterisks denote chiral carbon centers having a (S,S) absolute stereochemical configuration,

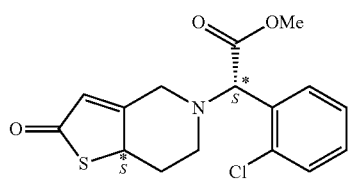

Formula IIA wherein the compound is isolated substantially free from its other isomers of formulas IIB, VI and VII, wherein the asterisks in Formula IIB denote chiral carbon centers;

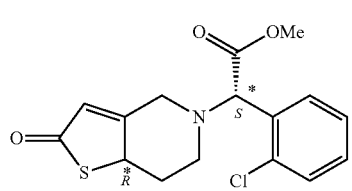

Formula IIB

-continued

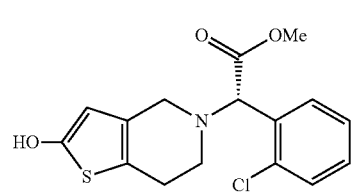

Formula VI

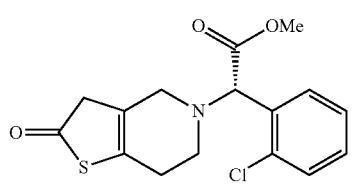

Formula VII and wherein said compound exhibits an X-ray powder diffraction pattern comprising peak reflections in a range starting at 22.22 and ending at 22.8 degrees 2θ; a range starting at 23.0 and ending at 23.6 degrees 2θ; and a range starting at 26.8 and ending at 27.2 degrees 2θ.

3. The compound of claim 2, wherein the other isomers of Formula IIB, VI or VII are individually or cumulatively less than 10% by weight of the total compound.

4. The compound of claim 2, wherein the other isomers of Formula IIB, VI and/or VII are less than 3% by weight of the total compound.

5. The compound of claim 2, wherein the other isomers of Formula IIB, VI and/or VII are less than 1.0% by weight of the total compound.

6. A composition comprising a solid form of substantially pure methyl (7aS,2'S)-2-(2-chlorophenyl)-2-(2,4,5,6,7,7a-hexahydrothieno[3,2-c]-5-pyridin-2-one)acetate that exhibits an X-ray powder diffraction pattern comprising peak reflections in a range starting at 22.22 and ending at 22.8 degrees 2θ; a range starting at 23.0 and ending at 23.6 degrees 2θ; and a range starting at 26.8 and ending at 27.2 degrees 2θ.

7. A solid form of substantially pure bisulfate salt of the compound of formula IIA, wherein the asterisks denote chiral carbon centers having a (S,S) absolute stereochemical configuration:

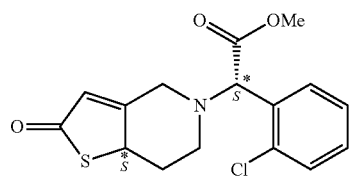

Formula IIA and wherein said compound exhibits an X-ray powder diffraction pattern comprising peak reflections in a range starting at 7.6 and ending at 8.1 degrees 2θ; a range starting at 21.7 and ending at 22.25 degrees 2θ; and a range starting at 23.75 and ending at 24.2 degrees 2θ.

8. A substantially pure solid bisulfate salt of the compound of formula IIA, wherein the asterisks denote chiral carbon centers having a (S,S) absolute stereochemical configuration,

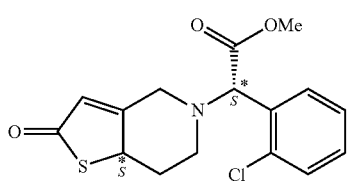

Formula IIA wherein the compound is isolated substantially free from its other isomers of formulas IIB, VI and VII, wherein the asterisks in Formula IIB denote chiral carbon centers:

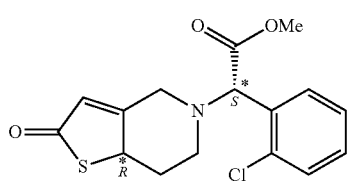

Formula IIB

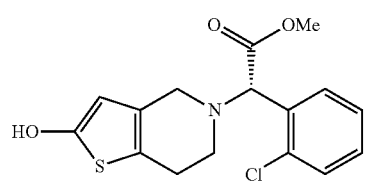

Formula VI

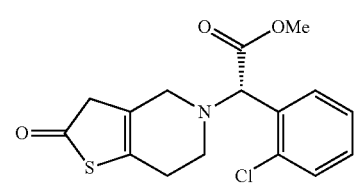

Formula VII and wherein said compound exhibits an X-ray powder diffraction pattern comprising peak reflections in a range starting at 7.6 and ending at 8.1 degrees 2θ; a range starting at 21.7 and ending at 22.25 degrees 2θ; and a range starting at 23.75 and ending at 24.2 degrees 2θ.

9. The compound of claim 8, wherein the other isomers of Formula IIB, VI or VII are individually or cumulatively less than 10% by weight of the total compound.

10. The compound of claim 8, wherein the other isomers of Formula IIB, VI and/or VII are less than 3% by weight of the total compound.

11. The compound of claim 8, wherein the other isomers of Formula IIB, VI and/or VII are less than 1.0% by weight of the total compound.

12. A composition comprising a solid form of substantially pure hydrogen sulfate salt of methyl(7aS,2'S)-2-(2-chlorophenyl)-2-(2,4,5,6,7,7a-hexahydrothieno[3,2-c]-5-pyridin-2-one)acetate that exhibits an X-ray powder diffraction pattern comprising peak reflections in a range starting at 7.6 and ending at 8.1 degrees 2θ; a range starting at 21.7 and ending at 22.25 degrees 2θ; and a range starting at 23.75 and ending at 24.2 degrees 2θ.

Figure 8:
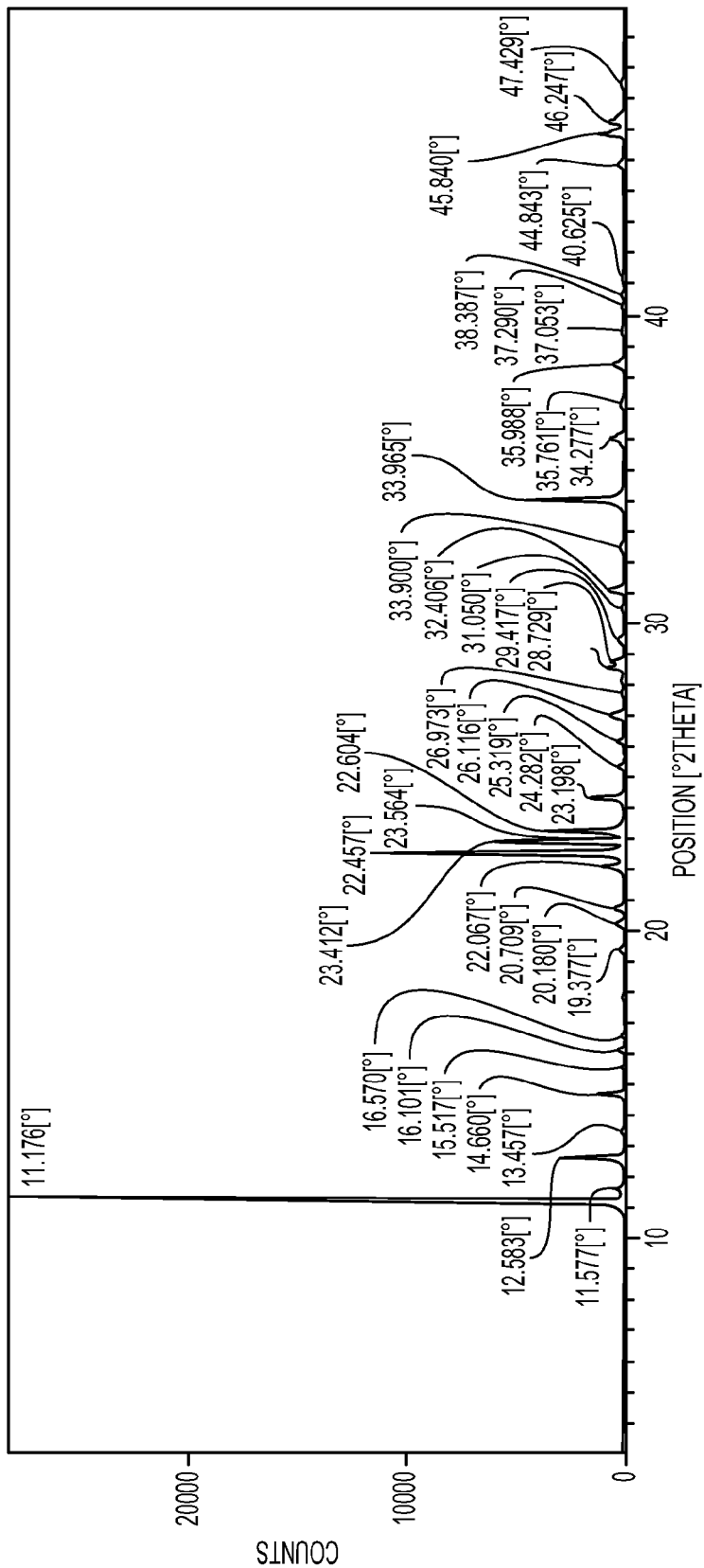
FIG. 8. A representative powder X-Ray diffraction pattern of substantially pure (7aS,2'S)-oxo-clopidogrel free base.

13. The solid form of substantially pure methyl (7aS,2'S)-2-(2-chlorophenyl)-2-(2,4,5,6,7,7a-hexahydrothieno[3,2-c]-5-pyridin-2-one)acetate of claim 1, characterized by having a X-Ray diffraction pattern substantially as shown in FIG. 8.

Figure 9:
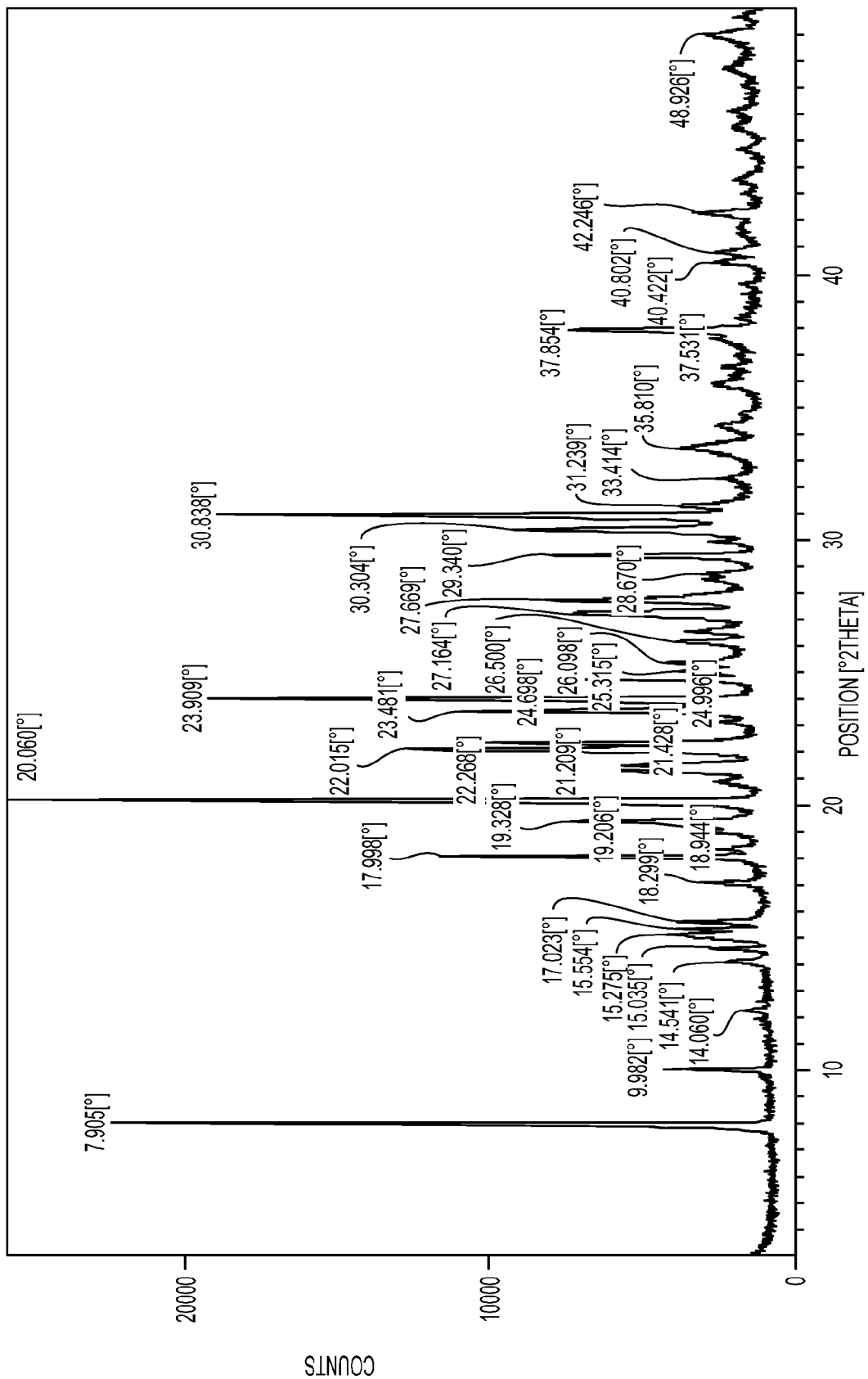
FIG. 9. A representative powder X-Ray diffraction pattern of (7aS,2'S)-oxo-clopidogrel bisulphate.
Figure 10:
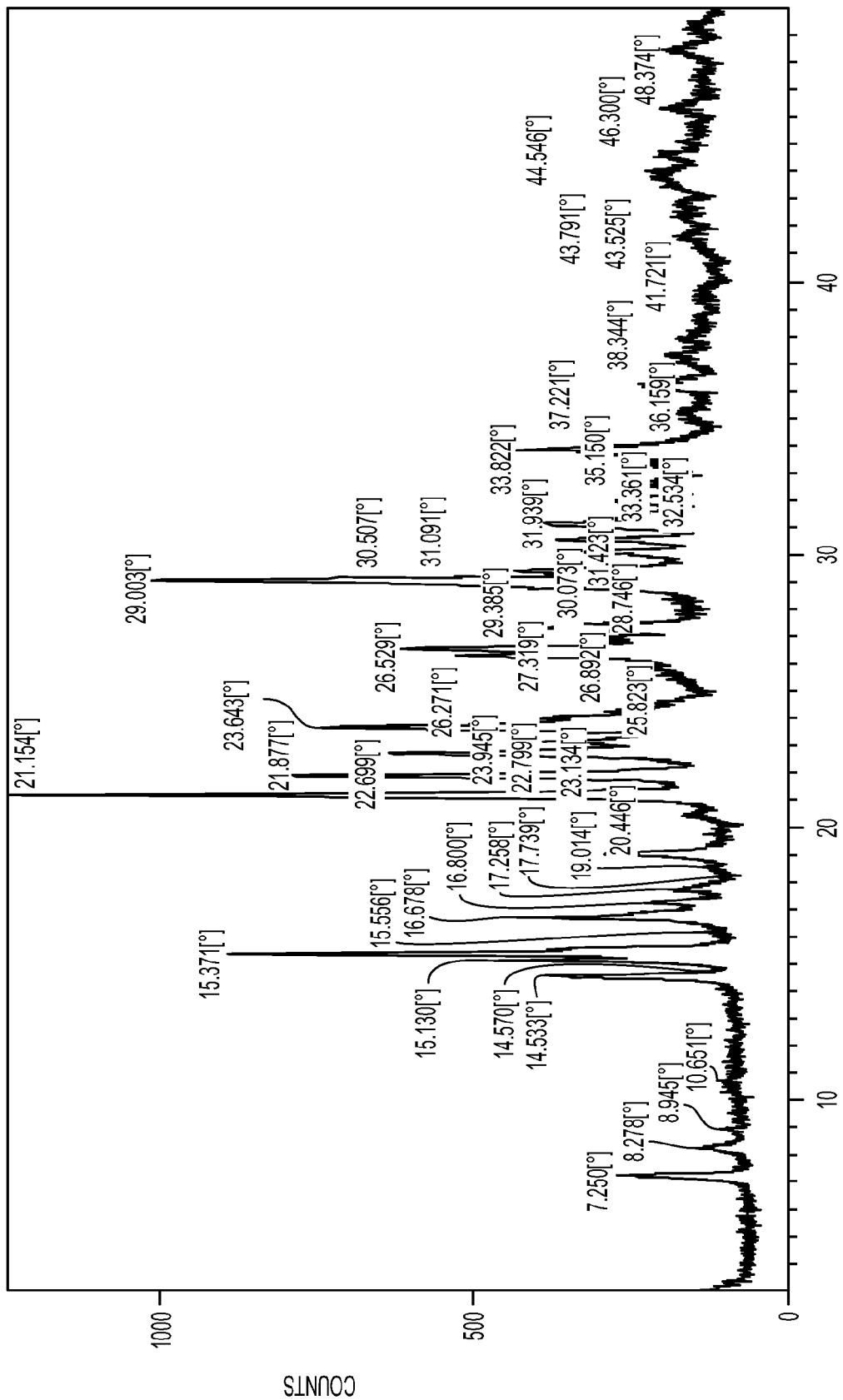
FIG. 10. A representative powder X-Ray diffraction pattern of (7aS,2'S)/(7aR,2'S)-oxo-clopidogrel hydrochloride.
Figure 11:
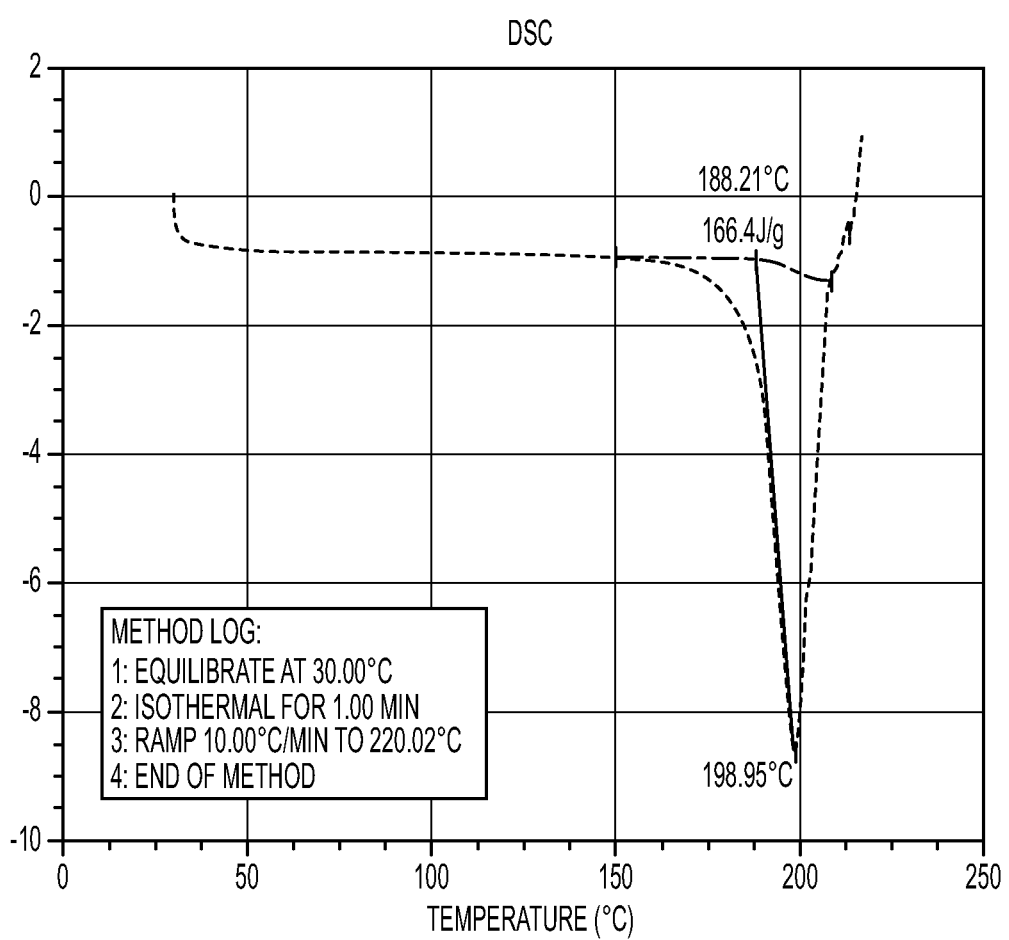
FIG. 11. A representative differential scanning calorimetric graph of (7aS,2'S)-oxo-clopidogrel bisulphate.

14. The solid form of substantially pure hydrogen sulfate salt of methyl (7aS,2'S)-2-(2-chlorophenyl)-2-(2,4,5,6,7,7a-hexahydrothieno[3,2-c]-5-pyridin-2-one)acetate of claim 7, characterized by having a X-Ray diffraction pattern substantially as shown in FIG. 9.

15. A pharmaceutical composition comprising a solid compound according to claim 1, 2, 7, or 8, and pharmaceutically acceptable excipients.

16. A pharmaceutical composition according to claim 15, wherein the composition further comprises one or more active compounds selected from the group consisting of aspirin, cilostazol, and dipyridamole.

* * * * *

UNITED STATES PATENT AND TRADEMARK OFFICE
CERTIFICATE OF CORRECTION

PATENT NO. : 8,536,337 B2  Page 1 of 1
APPLICATION NO. : 13/428657
DATED : September 17, 2013
INVENTOR(S) : Kumar et al.

It is certified that error appears in the above-identified patent and that said Letters Patent is hereby corrected as shown below:

Title Page insert

-- (30) Foreign Application Priority Data:

June 27, 2011   (IN) ......................1848/MUM/2011 --.

Signed and Sealed this
Third Day of December, 2013

Margaret A. Focarino
*Commissioner for Patents of the United States Patent and Trademark Office*